(12) United States Patent
Crawford et al.

(10) Patent No.: US 9,827,221 B2
(45) Date of Patent: *Nov. 28, 2017

(54) CRYSTALLINE SOLIDS OF A METAP-2 INHIBITOR AND METHODS OF MAKING AND USING SAME

(71) Applicant: Zafgen, Inc., Boston, MA (US)

(72) Inventors: Thomas Crawford, Essex, CT (US); Hayley A. Reece, Edinburgh (GB)

(73) Assignee: Zafgen, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/145,403

(22) Filed: May 3, 2016

(65) Prior Publication Data

US 2017/0087119 A1    Mar. 30, 2017

Related U.S. Application Data

(63) Continuation of application No. 14/178,788, filed on Feb. 12, 2014, now Pat. No. 9,371,312, which is a continuation of application No. 13/679,310, filed on Nov. 16, 2012, now Pat. No. 8,735,447, which is a continuation of application No. 13/568,476, filed on Aug. 7, 2012, now Pat. No. 8,349,891, which is a continuation of application No. PCT/US2011/059966, filed on Nov. 9, 2011.

(60) Provisional application No. 61/411,655, filed on Nov. 9, 2010.

(51) Int. Cl.
*A61K 31/336*    (2006.01)

(52) U.S. Cl.
CPC .................................. *A61K 31/336* (2013.01)

(58) Field of Classification Search
CPC ... C07D 407/04; C07D 407/08; C07D 303/16
See application file for complete search history.

(56) References Cited

U.S. PATENT DOCUMENTS

| | | |
|---|---|---|
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,196,406 A | 3/1993 | Kamei et al. |
| 5,204,345 A | 4/1993 | Kishimoto et al. |
| 5,288,722 A | 2/1994 | Kishimoto et al. |
| 5,290,807 A | 3/1994 | Folkman et al. |
| 5,422,363 A | 6/1995 | Yanai et al. |
| 5,536,623 A | 7/1996 | Ohmachi et al. |

(Continued)

FOREIGN PATENT DOCUMENTS

| | | |
|---|---|---|
| EP | 0682020 A1 | 11/1995 |
| WO | WO-1999/059986 A1 | 11/1999 |

(Continued)

OTHER PUBLICATIONS

Anderson, Hamilton H., "The Use of Fumagillin in Amoebiasis," *Annals New York Academy of Sciences*, 1118-1124. (1952).

(Continued)

*Primary Examiner* — Jianfeng Song
(74) *Attorney, Agent, or Firm* — Goodwin Procter LLP

(57) ABSTRACT

The disclosure is in part directed to crystalline forms of 6-O-(4-dimethylaminoethoxy)cinnamoyl fumagillol and variants thereof.

7 Claims, 21 Drawing Sheets

(56) References Cited

U.S. PATENT DOCUMENTS

| | | |
|---|---|---|
| 5,698,586 A | 12/1997 | Kishimoto et al. |
| 5,767,293 A | 6/1998 | Oku et al. |
| 5,846,562 A | 12/1998 | Yanai et al. |
| 5,900,431 A | 5/1999 | Molina et al. |
| 6,017,949 A | 1/2000 | D'Amato et al. |
| 6,017,954 A | 1/2000 | Folkman et al. |
| 6,040,337 A | 3/2000 | Hong, II et al. |
| 6,063,812 A | 5/2000 | Hong et al. |
| 6,180,626 B1 | 1/2001 | Shimomura et al. |
| 6,207,704 B1 | 3/2001 | Liu et al. |
| 6,306,819 B1 | 10/2001 | Rupnick et al. |
| 6,323,228 B1 | 11/2001 | BaMaung et al. |
| 6,383,471 B1 | 5/2002 | Chen et al. |
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Eustache et al. |
| 7,084,108 B2 | 8/2006 | Olson et al. |
| 7,268,111 B2 | 9/2007 | Olson et al. |
| 7,718,695 B2 | 5/2010 | Kim et al. |
| 8,349,891 B2 | 1/2013 | Crawford et al. |
| 8,735,447 B2 | 5/2014 | Crawford et al. |
| 9,371,312 B2 | 6/2016 | Crawford et al. |
| 2004/0067266 A1 | 4/2004 | Toppo |
| 2004/0204472 A1 | 10/2004 | Briggs et al. |
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2012/0034233 A1 | 2/2012 | Hughes et al. |

FOREIGN PATENT DOCUMENTS

| | | |
|---|---|---|
| WO | WO-1999/059987 | 11/1999 |
| WO | WO-2000/064876 A1 | 11/2000 |
| WO | WO-2003/027104 A1 | 4/2003 |
| WO | WO-2004/033419 A1 | 4/2004 |
| WO | WO-2005/082349 A1 | 9/2005 |
| WO | WO-2005082349 * | 9/2005 |
| WO | WO-2006/080591 A1 | 8/2006 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |

OTHER PUBLICATIONS

Benny, Ofra, et al., (2008) "An Orally Delivered Small-Molecule Formulation with Antiangiogenic and Anticancer Activity," Nature Biotechnology, 26, 7:799-807.

Bernier et al. (2005) "Fumagillin class inhibitors of methionine aminopeptidase-2," Drugs of the Future 30(5): 497-500.

Brakenhielm, E., et al., (2004) "Angiogenesis Inhibitor, TNP-470, Prevents Diet-Induced and Genetic Obesity in Mice," Circulation Research, http://circres.ahajournals.org (accessed on Feb. 8, 2007).

Braunwald, et al.. "Obesity" in Harrison's Principles of Internal Medicine, 15th Ed., 479-86 (2001).

DiPaolo, J.A., et al. (1958-1959) "Studies on the Carcinolytic Activity of Fumagillin and Some of its Derivatives," Antibiotics Annual, 541-548.

Drevs, Joachim, et al. (2003) "Antiangiogenic Potency of FK866/ K22.175, a New Inhibitor of Intracellular NAD Biosynthesis, In Murine Renal Cell Carcinoma," Anticancer Research 23: 4853-4858.

Dumas, J., et al., "Synthesis and Structure Activity Relationships of Novel Small Molecule Cathepsin D Inhibitors," Bioorganic & Medicinal Chemistry Letters 9 (1999) 2531-2536.

Eder, JP, et al., (2006) "Phase 1 Dose Escalation Safety & Tolerance Study of PPI-2458 in Subjects with Non-Hodgkin's Lymphoma or Solid Tumors," (Presented on Nov. 7-10, 2006 at EORTC-NCI-AACR Symposium on "Molecular Targets and Cancer Therapeutics.").

European Search Report for EP 09798793 dated Oct. 11, 2011, 9 pages.

Everhart (1993) "Contributions of Obesity and Weight Loss to Gallstone Disease," Ann Intern Med. 119:1029-1035.

Hughes et al. "Ascending dose-controlled trial of beloranib, a novel obesity treatment for safety, tolerability, and weight loss in obese women" Obesity (Silver Spring). Sep. 2013;21(9):1785-8 doi: 10.1002/oby.20356. Epub May 25, 2013.

Ingber et al. (1990) "Synthetic analogues of fumagillin that inhibit angiogenesis and suppress tumour growth," Nature 348: 555-557.

Jeong, et al., "Total Synthesis and Antiangiogenic Activity of Cyclopentane Analogues of Fumagillol," Bioorg. Med. Chem. Lett. 15 3580-83 (2005).

Kim, YM, et al. (2007) "Assessment of the Anti-Obesity Effects of the TNP-470 Analog, CKD-732," Journal of Molecular Endocrinology 38, 455-465.

Kruger, Erwin, A., (2000) "TNP-470: An Angiogenesis Inhibitor in Clinical Development for Cancer," Exp. Opin. Invest. Drugs 9(6), pp. 1383-1396.

Molina et al. (2002) "Fumagillin Treatment of Intestinal Microsporidiosis," N. Engl. J. Med. 346(25): 1963-1969.

Molina et al. (1997) "Potential Efficacy of Fumagillin in Intestinal Microsporidiosis Due to Enterocytozoon Bieneusi in Patients with HIV Infection: Results of a Drug Screening Study," AIDS, 11:1603-1610.

Molina, et al.(2000) "Trial of Oral Fumagillin for the Treatment of Intestinal Microsporidiosis in Patients with HIV Infection," AIDS, 14:1341-1348.

Naganuma, Yasuko, et al. (2011) "Metronomic Doxifluridine Chemotherapy Combined with the Anti-Angiogenic Agent TNP=470 Inhibits the Growth of Human Uterine Carcinosarcoma Xenografts," Cancer Sci 102(8): pp. 1545-1552.

National Task Force on the Prevention and Treatment of Obesity (1993) "Very Low-Calorie Diets," JAMA 270(8):967-974.

Noel et al. (2009) "Increased Risk of Acute Pancreatitis and Biliary Disease Observed in Patients with Type 2 Diabetes," Diabetes Care 32(5):834-838.

Pagliarulo et al. (2003) "Gallstone disease and related risk factors in a large cohort of diabetic patients," Digestive and Liver Disease 36:130-134.

Picoul et al. (2003) "Progress in fumagillin synthesis," Pure Appl. Chem. 75(2-3): 235-249.

Rupnick, MA (2002) "Adipose Tissue Mass Can be Regulated Through the Vasculature," PNA 99, 10730-10735.

Search Report completed on Mar. 2, 2011, for International Application PCT/US2010/052050.

Seneca et al. (1956) "Amebiasis: a review. II. Laboratory diagnosis, differential diagnosis and therapy," Am J. Digestive Dis. 1: 310-322.

Shin, SJ (2010) "A Phase I Pharmacokinetic and Pharmacodynamic Stdy of CKD-732, an Antiangiogenic Agent, in Patients with Refractory Solid Cancer," Invest New Drugs 28:650-658, (2010) Published online Dec. 29, 2010.

Weinsier et al. (1993) "Gallstone Formation and Weight Loss," Obesity Research 1(1):51-56.

Weinsier, et al. (1995) "Medically Safe Rate of Weight Loss for the Treatment of Obesity: A Guideline Based on Risk of Gallstone Formation," The American Journal of Medicine 98:115-117.

Winter et al. (2006) "Endothelial $\alpha_v\beta_3$ Integrin-Targeted Fumagillin Nanoparticles Inhibit Angiogenesis in Atherosclerosis," Arterioscler Thromb Vasc Biol.: 2103-2109.

Yanai, Shigeo, et al. (1995) "Antitumor Effect of Arterial Administration of a Medium-Chain Triglyceride Solutionof an Angiogenesis Inhibitor, TNP-470, in Rabbits Bearing VX-2 Carcinoma," Pharmaceutical Research 12(5): pp. 653-657.

Yanai, Shigeo, et al., (1994) "Antitumor Activity of a Medium-Chain Triglyceride Solution of the Angiogenesis Inhibitor TNP-470 (AGM-1470) when Administered via the Hepatic Artery to Rats

(56) References Cited

OTHER PUBLICATIONS

Bearing Walker 256 Carcinosarcoma in the Liver," The Journal of Pharmacology and Experimental Therapeutics 271(3): pp. 1267-1273.

* cited by examiner

Form A $^1$H NMR SPECTRUM OF FORM A

Form A

FIG. 12C

Atomic coordinates:

| Atom | x | y | z | U$_{iso/equiv}$ |
|---|---|---|---|---|
| C1 | −0.1127(18) | 1.1185(7) | 1.1007(2) | 0.094(3) |
| C2 | −0.3725(17) | 1.2183(9) | 1.0646(4) | 0.136(5) |
| N1 | −0.1933(13) | 1.1504(5) | 1.06128(19) | 0.092(2) |
| C3 | −0.2113(16) | 1.0738(7) | 1.0352(2) | 0.060(2) |
| C4 | 0.0287(14) | 1.0412(6) | 1.02090(16) | 0.089(3) |
| N1' | −0.1933(13) | 1.1504(5) | 1.06128(19) | 0.092(2) |
| C3' | −0.086(4) | 1.1506(17) | 1.0236(5) | 0.060(2) |
| C4' | 0.0287(14) | 1.0412(6) | 1.02090(16) | 0.089(3) |
| O1 | −0.0318(7) | 0.9727(4) | 0.99048(9) | 0.0640(12) |
| C5 | 0.1200(8) | 0.9063(4) | 0.97610(12) | 0.0402(10) |
| C6 | 0.0536(8) | 0.8492(4) | 0.94357(12) | 0.0376(9) |
| C7 | 0.1931(7) | 0.7804(3) | 0.92688(11) | 0.0328(8) |
| C8 | 0.4015(7) | 0.7685(3) | 0.94139(10) | 0.0295(8) |
| C9 | 0.4625(7) | 0.8252(3) | 0.97435(10) | 0.0316(8) |
| C10 | 0.3234(8) | 0.8950(3) | 0.99168(11) | 0.0347(9) |
| C11 | 0.5571(7) | 0.7016(3) | 0.92295(12) | 0.0343(9) |
| C12 | 0.5384(8) | 0.6466(3) | 0.88989(12) | 0.0357(9) |
| O2 | 0.8898(7) | 0.5771(3) | 0.89201(10) | 0.0578(11) |
| C13 | 0.7224(8) | 0.5875(4) | 0.87535(12) | 0.0395(10) |
| O3 | 0.6792(5) | 0.5470(2) | 0.83956(7) | 0.0330(6) |
| C14 | 0.8585(7) | 0.4973(3) | 0.81960(11) | 0.0322(8) |
| C15 | 0.7599(6) | 0.4229(3) | 0.78977(10) | 0.0265(7) |
| O4 | 0.6306(5) | 0.3479(2) | 0.80816(8) | 0.0315(6) |
| C16 | 0.6204(6) | 0.4779(3) | 0.75913(10) | 0.0244(7) |
| C17 | 0.7485(6) | 0.5638(3) | 0.73992(11) | 0.0277(7) |
| O5 | 0.8823(5) | 0.5355(2) | 0.70669(8) | 0.0328(6) |
| C18 | 0.8583(7) | 0.6342(3) | 0.76912(12) | 0.0343(8) |
| C19 | 0.9929(7) | 0.5762(3) | 0.79856(12) | 0.0360(9) |
| C20 | 0.7511(9) | 0.2702(3) | 0.82708(15) | 0.0450(11) |
| C21 | 0.7026(7) | 0.6041(3) | 0.70070(12) | 0.0352(9) |
| C22 | 0.5198(6) | 0.4023(3) | 0.73014(10) | 0.0244(7) |
| O6 | 0.3053(4) | 0.3699(2) | 0.74204(8) | 0.0286(6) |
| C23 | 0.6613(7) | 0.3168(3) | 0.71524(11) | 0.0304(8) |
| C24 | 0.3266(6) | 0.4348(3) | 0.70809(10) | 0.0263(7) |
| C25 | 0.2617(7) | 0.3923(3) | 0.66842(11) | 0.0319(8) |
| C26 | 0.3771(7) | 0.4465(3) | 0.63557(11) | 0.0338(8) |
| C27 | 0.3002(7) | 0.5187(3) | 0.61231(11) | 0.0353(9) |
| C28 | 0.0725(8) | 0.5565(4) | 0.61362(13) | 0.0421(11) |
| C29 | 0.4372(9) | 0.5661(4) | 0.58149(12) | 0.0467(12) |
| H1A | −0.1046 | 1.178 | 1.1181 | 0.14 |
| H1B | 0.0304 | 1.0883 | 1.0979 | 0.14 |
| H1C | −0.2107 | 1.068 | 1.1121 | 0.14 |
| H2A | −0.3422 | 1.2698 | 1.0849 | 0.204 |
| H2B | −0.5006 | 1.1796 | 1.0721 | 0.204 |
| H2C | −0.3972 | 1.252 | 1.0392 | 0.204 |
| H3A | −0.2975 | 1.096 | 1.0122 | 0.072 |

FIG. 12C Cont.

| | | | | |
|---|---|---|---|---|
| H3B | -0.2842 | 1.0149 | 1.0476 | 0.072 |
| H4A | 0.1114 | 1.0999 | 1.0107 | 0.107 |
| H4B | 0.1106 | 1.0069 | 1.0421 | 0.107 |
| H3'1 | 0.0207 | 1.2062 | 1.0222 | 0.072 |
| H3'2 | -0.1909 | 1.1593 | 1.0019 | 0.072 |
| H4'1 | 0.1849 | 1.0532 | 1.0184 | 0.107 |
| H4'2 | 0.0055 | 1.0061 | 1.0464 | 0.107 |
| H6 | -0.0866 | 0.8577 | 0.9331 | 0.045 |
| H7 | 0.1471 | 0.7403 | 0.9051 | 0.039 |
| H9 | 0.6018 | 0.816 | 0.9852 | 0.038 |
| H10 | 0.3675 | 0.9341 | 1.0138 | 0.042 |
| H11 | 0.691 | 0.6961 | 0.9362 | 0.041 |
| H12 | 0.4065 | 0.6457 | 0.8758 | 0.043 |
| H14 | 0.9482 | 0.4593 | 0.8392 | 0.039 |
| H15 | 0.8793 | 0.3876 | 0.7755 | 0.032 |
| H16 | 0.4996 | 0.5106 | 0.7739 | 0.029 |
| H18A | 0.9508 | 0.6827 | 0.7546 | 0.041 |
| H18B | 0.7482 | 0.6742 | 0.7834 | 0.041 |
| H19A | 1.0541 | 0.6243 | 0.8181 | 0.043 |
| H19B | 1.1132 | 0.5423 | 0.7847 | 0.043 |
| H20A | 0.653 | 0.2208 | 0.8391 | 0.067 |
| H20B | 0.8419 | 0.3005 | 0.8476 | 0.067 |
| H20C | 0.8416 | 0.2355 | 0.8076 | 0.067 |
| H21A | 0.5752 | 0.5772 | 0.6867 | 0.042 |
| H21B | 0.7346 | 0.6768 | 0.6957 | 0.042 |
| H23A | 0.7807 | 0.3064 | 0.7336 | 0.046 |
| H23B | 0.718 | 0.3346 | 0.6891 | 0.046 |
| H23C | 0.5769 | 0.2539 | 0.7133 | 0.046 |
| H24 | 0.2834 | 0.5073 | 0.7126 | 0.032 |
| H25A | 0.2958 | 0.3186 | 0.6674 | 0.038 |
| H25B | 0.1049 | 0.4002 | 0.6649 | 0.038 |
| H26 | 0.5215 | 0.4265 | 0.631 | 0.041 |
| H28A | 0.0527 | 0.6098 | 0.5937 | 0.063 |
| H28B | 0.042 | 0.5845 | 0.6399 | 0.063 |
| H28C | -0.0256 | 0.4998 | 0.6082 | 0.063 |
| H29A | 0.3541 | 0.6175 | 0.5671 | 0.07 |
| H29B | 0.4864 | 0.5134 | 0.563 | 0.07 |
| H29C | 0.5616 | 0.5985 | 0.594 | 0.07 |

Anisotropic displacement parameters:

| Atom | $u^{11}$ | $u^{22}$ | $u^{33}$ | $u^{12}$ | $u^{13}$ | $u^{23}$ |
|---|---|---|---|---|---|---|
| C1 | 0.122(7) | 0.090(5) | 0.069(4) | 0.010(6) | 0.001(5) | -0.012(4) |
| C2 | 0.085(7) | 0.138(8) | 0.184(11) | 0.054(7) | -0.004(7) | -0.070(8) |
| N1 | 0.112(6) | 0.077(4) | 0.086(4) | 0.053(4) | 0.038(4) | 0.010(3) |
| C3 | 0.066(5) | 0.071(5) | 0.043(3) | 0.027(4) | -0.015(3) | -0.023(3) |
| C4 | 0.125(6) | 0.106(5) | 0.037(2) | 0.085(5) | -0.022(3) | -0.032(3) |
| N1' | 0.112(6) | 0.077(4) | 0.086(4) | 0.053(4) | 0.038(4) | 0.010(3) |
| C3' | 0.066(5) | 0.071(5) | 0.043(3) | 0.027(4) | -0.015(3) | -0.023(3) |
| C4' | 0.125(6) | 0.106(5) | 0.037(2) | 0.085(5) | -0.022(3) | -0.032(3) |

FIG. 12C Cont.

| | | | | | | |
|---|---|---|---|---|---|---|
| O1 | 0.061(2) | 0.099(3) | 0.0319(15) | 0.046(2) | -0.0023(16) | -0.0104(18) |
| C5 | 0.047(3) | 0.049(2) | 0.0251(16) | 0.013(2) | 0.0076(18) | 0.0025(16) |
| C6 | 0.033(2) | 0.052(2) | 0.0282(17) | 0.003(2) | 0.0048(16) | 0.0066(17) |
| C7 | 0.037(2) | 0.0367(19) | 0.0251(16) | -0.0071(18) | -0.0005(15) | 0.0001(15) |
| C8 | 0.034(2) | 0.0314(18) | 0.0230(15) | -0.0049(16) | 0.0025(15) | -0.0031(14) |
| C9 | 0.034(2) | 0.0379(19) | 0.0234(15) | -0.0032(17) | 0.0010(15) | -0.0043(15) |
| C10 | 0.041(2) | 0.040(2) | 0.0231(15) | 0.0066(19) | 0.0024(16) | -0.0031(15) |
| C11 | 0.036(2) | 0.036(2) | 0.0307(18) | -0.0010(18) | 0.0003(16) | -0.0057(15) |
| C12 | 0.036(2) | 0.040(2) | 0.0312(18) | -0.0021(19) | -0.0014(17) | -0.0096(16) |
| O2 | 0.049(2) | 0.076(2) | 0.0479(18) | 0.017(2) | -0.0205(17) | -0.0357(18) |
| C13 | 0.042(2) | 0.043(2) | 0.035(2) | -0.002(2) | -0.0025(18) | -0.0178(17) |
| O3 | 0.0317(14) | 0.0404(14) | 0.0270(12) | 0.0019(13) | -0.0009(12) | -0.0114(11) |
| C14 | 0.030(2) | 0.0346(18) | 0.0321(17) | 0.0033(17) | -0.0020(16) | -0.0124(15) |
| C15 | 0.0225(17) | 0.0301(17) | 0.0270(16) | 0.0051(15) | -0.0022(14) | -0.0062(13) |
| O4 | 0.0359(15) | 0.0277(12) | 0.0309(12) | 0.0040(12) | -0.0059(12) | 0.0007(10) |
| C16 | 0.0220(16) | 0.0238(15) | 0.0274(15) | 0.0017(14) | -0.0017(13) | -0.0055(13) |
| C17 | 0.0235(17) | 0.0260(16) | 0.0335(17) | 0.0034(15) | 0.0028(15) | -0.0065(14) |
| O5 | 0.0279(13) | 0.0406(15) | 0.0299(12) | 0.0069(13) | 0.0035(11) | -0.0020(11) |
| C18 | 0.031(2) | 0.0310(18) | 0.041(2) | -0.0042(17) | 0.0030(17) | -0.0109(16) |
| C19 | 0.029(2) | 0.042(2) | 0.0371(19) | -0.0030(18) | -0.0038(17) | -0.0141(17) |
| C20 | 0.054(3) | 0.032(2) | 0.049(2) | 0.009(2) | -0.015(2) | 0.0018(19) |
| C21 | 0.029(2) | 0.0306(18) | 0.046(2) | 0.0002(17) | -0.0042(17) | 0.0026(16) |
| C22 | 0.0218(17) | 0.0267(16) | 0.0247(15) | 0.0029(14) | 0.0012(13) | -0.0038(13) |
| O6 | 0.0240(13) | 0.0326(13) | 0.0293(12) | -0.0030(11) | 0.0013(10) | -0.0025(10) |
| C23 | 0.031(2) | 0.0294(17) | 0.0311(17) | 0.0065(16) | -0.0016(15) | -0.0122(14) |
| C24 | 0.0231(17) | 0.0296(17) | 0.0263(15) | -0.0011(15) | -0.0001(14) | -0.0036(13) |
| C25 | 0.028(2) | 0.0386(19) | 0.0289(17) | 0.0009(17) | -0.0056(15) | -0.0053(15) |
| C26 | 0.0281(19) | 0.045(2) | 0.0281(17) | -0.0012(18) | -0.0024(15) | -0.0081(16) |
| C27 | 0.038(2) | 0.042(2) | 0.0259(16) | -0.0026(19) | -0.0048(16) | -0.0090(16) |
| C28 | 0.047(3) | 0.044(2) | 0.035(2) | 0.009(2) | -0.0111(19) | -0.0067(18) |
| C29 | 0.060(3) | 0.052(3) | 0.0278(18) | -0.009(2) | -0.002(2) | -0.0013(18) |

Bond lengths:

| | | | |
|---|---|---|---|
| C1-N1 | 1.487(10) | C15-H15 | 1 |
| C1-H1A | 0.98 | O4-C20 | 1.420(5) |
| C1-H1B | 0.98 | C16-C17 | 1.527(5) |
| C1-H1C | 0.98 | C16-C22 | 1.529(5) |
| C2-N1 | 1.433(10) | C16-H16 | 1 |
| C2-H2A | 0.98 | C17-O5 | 1.449(4) |
| C2-H2B | 0.98 | C17-C21 | 1.457(5) |
| C2-H2C | 0.98 | C17-C18 | 1.516(5) |
| N1-C3 | 1.344(10) | O5-C21 | 1.451(5) |
| C3-C4 | 1.629(12) | C18-C19 | 1.509(6) |
| C3-H3A | 0.99 | C18-H18A | 0.99 |
| C3-H3B | 0.99 | C18-H18B | 0.99 |
| C4-O1 | 1.418(7) | C19-H19A | 0.99 |
| C4-H4A | 0.99 | C19-H19B | 0.99 |
| C4-H4B | 0.99 | C20-H20A | 0.98 |
| C3'-H3'1 | 0.99 | C20-H20B | 0.98 |

FIG.12C Cont.

| | | | |
|---|---|---|---|
| C3'-H3'2 | 0.99 | C20-H20C | 0.98 |
| O1-C5 | 1.375(6) | C21-H21A | 0.99 |
| C5-C10 | 1.382(7) | C21-H21B | 0.99 |
| C5-C6 | 1.395(6) | C22-O6 | 1.460(5) |
| C6-C7 | 1.375(6) | C22-C24 | 1.479(5) |
| C6-H6 | 0.95 | C22-C23 | 1.514(5) |
| C7-C8 | 1.397(6) | O6-C24 | 1.436(4) |
| C7-H7 | 0.95 | C23-H23A | 0.98 |
| C8-C9 | 1.394(5) | C23-H23B | 0.98 |
| C8-C11 | 1.450(6) | C23-H23C | 0.98 |
| C9-C10 | 1.390(6) | C24-C25 | 1.509(5) |
| C9-H9 | 0.95 | C24-H24 | 1 |
| C10-H10 | 0.95 | C25-C26 | 1.503(6) |
| C11-C12 | 1.337(5) | C25-H25A | 0.99 |
| C11-H11 | 0.95 | C25-H25B | 0.99 |
| C12-C13 | 1.470(6) | C26-C27 | 1.322(6) |
| C12-H12 | 0.95 | C26-H26 | 0.95 |
| O2-C13 | 1.194(6) | C27-C29 | 1.484(6) |
| C13-O3 | 1.350(5) | C27-C28 | 1.504(7) |
| O3-C14 | 1.459(5) | C28-H28A | 0.98 |
| C14-C19 | 1.511(6) | C28-H28B | 0.98 |
| C14-C15 | 1.533(5) | C28-H28C | 0.98 |
| C14-H14 | 1 | C29-H29A | 0.98 |
| C15-O4 | 1.415(5) | C29-H29B | 0.98 |
| C15-C16 | 1.534(5) | C29-H29C | 0.98 |

Bond angles:

| | | | |
|---|---|---|---|
| N1-C1-H1A | 109.5 | C15-C16-H16 | 106.9 |
| N1-C1-H1B | 109.5 | O5-C17-C21 | 59.9(2) |
| H1A-C1-H1B | 109.5 | O5-C17-C18 | 113.7(3) |
| N1-C1-H1C | 109.5 | C21-C17-C18 | 117.5(3) |
| H1A-C1-H1C | 109.5 | O5-C17-C16 | 116.3(3) |
| H1B-C1-H1C | 109.5 | C21-C17-C16 | 123.6(3) |
| N1-C2-H2A | 109.5 | C18-C17-C16 | 114.1(3) |
| N1-C2-H2B | 109.5 | C17-O5-C21 | 60.3(2) |
| H2A-C2-H2B | 109.5 | C19-C18-C17 | 112.0(3) |
| N1-C2-H2C | 109.5 | C19-C18-H18A | 109.2 |
| H2A-C2-H2C | 109.5 | C17-C18-H18A | 109.2 |
| H2B-C2-H2C | 109.5 | C19-C18-H18B | 109.2 |
| C3-N1-C2 | 116.9(8) | C17-C18-H18B | 109.2 |
| C3-N1-C1 | 114.1(6) | H18A-C18-H18B | 107.9 |
| C2-N1-C1 | 111.6(7) | C18-C19-C14 | 110.4(4) |
| N1-C3-C4 | 108.3(7) | C18-C19-H19A | 109.6 |
| N1-C3-H3A | 110 | C14-C19-H19A | 109.6 |
| C4-C3-H3A | 110 | C18-C19-H19B | 109.6 |
| N1-C3-H3B | 110 | C14-C19-H19B | 109.6 |
| C4-C3-H3B | 110 | H19A-C19-H19B | 108.1 |
| H3A-C3-H3B | 108.4 | O4-C20-H20A | 109.5 |
| O1-C4-C3 | 97.9(6) | O4-C20-H20B | 109.5 |

FIG.12C Cont.

| | | | |
|---|---|---|---|
| O1-C4-H4A | 112.2 | H20A-C20-H20B | 109.5 |
| C3-C4-H4A | 112.2 | O4-C20-H20C | 109.5 |
| O1-C4-H4B | 112.2 | H20A-C20-H20C | 109.5 |
| C3-C4-H4B | 112.2 | H20B-C20-H20C | 109.5 |
| H4A-C4-H4B | 109.8 | O5-C21-C17 | 59.8(2) |
| H3'1-C3'-H3'2 | 108.9 | O5-C21-H21A | 117.8 |
| C5-O1-C4 | 118.4(5) | C17-C21-H21A | 117.8 |
| O1-C5-C10 | 124.4(4) | O5-C21-H21B | 117.8 |
| O1-C5-C6 | 114.6(4) | C17-C21-H21B | 117.8 |
| C10-C5-C6 | 121.0(4) | H21A-C21-H21B | 114.9 |
| C7-C6-C5 | 119.3(4) | O6-C22-C24 | 58.5(2) |
| C7-C6-H6 | 120.3 | O6-C22-C23 | 114.2(3) |
| C5-C6-H6 | 120.3 | C24-C22-C23 | 121.3(3) |
| C6-C7-C8 | 121.1(4) | O6-C22-C16 | 112.8(3) |
| C6-C7-H7 | 119.4 | C24-C22-C16 | 118.1(3) |
| C8-C7-H7 | 119.4 | C23-C22-C16 | 117.1(3) |
| C9-C8-C7 | 118.4(4) | C24-O6-C22 | 61.4(2) |
| C9-C8-C11 | 119.0(4) | C22-C23-H23A | 109.5 |
| C7-C8-C11 | 122.6(4) | C22-C23-H23B | 109.5 |
| C10-C9-C8 | 121.3(4) | H23A-C23-H23B | 109.5 |
| C10-C9-H9 | 119.4 | C22-C23-H23C | 109.5 |
| C8-C9-H9 | 119.4 | H23A-C23-H23C | 109.5 |
| C5-C10-C9 | 118.8(4) | H23B-C23-H23C | 109.5 |
| C5-C10-H10 | 120.6 | O6-C24-C22 | 60.1(2) |
| C9-C10-H10 | 120.6 | O6-C24-C25 | 117.9(3) |
| C12-C11-C8 | 129.0(4) | C22-C24-C25 | 124.1(3) |
| C12-C11-H11 | 115.5 | O6-C24-H24 | 114.5 |
| C8-C11-H11 | 115.5 | C22-C24-H24 | 114.5 |
| C11-C12-C13 | 119.8(4) | C25-C24-H24 | 114.5 |
| C11-C12-H12 | 120.1 | C26-C25-C24 | 110.8(3) |
| C13-C12-H12 | 120.1 | C26-C25-H25A | 109.5 |
| O2-C13-O3 | 123.6(4) | C24-C25-H25A | 109.5 |
| O2-C13-C12 | 125.8(4) | C26-C25-H25B | 109.5 |
| O3-C13-C12 | 110.6(4) | C24-C25-H25B | 109.5 |
| C13-O3-C14 | 116.0(3) | H25A-C25-H25B | 108.1 |
| O3-C14-C19 | 109.7(3) | C27-C26-C25 | 127.3(4) |
| O3-C14-C15 | 106.4(3) | C27-C26-H26 | 116.3 |
| C19-C14-C15 | 110.4(3) | C25-C26-H26 | 116.3 |
| O3-C14-H14 | 110.1 | C26-C27-C29 | 120.7(4) |
| C19-C14-H14 | 110.1 | C26-C27-C28 | 124.1(4) |
| C15-C14-H14 | 110.1 | C29-C27-C28 | 115.2(4) |
| O4-C15-C14 | 112.4(3) | C27-C28-H28A | 109.5 |
| O4-C15-C16 | 107.5(3) | C27-C28-H28B | 109.5 |
| C14-C15-C16 | 111.9(3) | H28A-C28-H28B | 109.5 |
| O4-C15-H15 | 108.3 | C27-C28-H28C | 109.5 |
| C14-C15-H15 | 108.3 | H28A-C28-H28C | 109.5 |
| C16-C15-H15 | 108.3 | H28B-C28-H28C | 109.5 |
| C15-O4-C20 | 113.4(3) | C27-C29-H29A | 109.5 |
| C17-C16-C22 | 114.8(3) | C27-C29-H29B | 109.5 |
| C17-C16-C15 | 109.8(3) | H29A-C29-H29B | 109.5 |

FIG. 12C Cont.

| | | | |
|---|---|---|---|
| C22-C16-C15 | 111.2(3) | C27-C29-H29C | 109.5 |
| C17-C16-H16 | 106.9 | H29A-C29-H29C | 109.5 |
| C22-C16-H16 | 106.9 | H29B-C29-H29C | 109.5 |

Torsion angles:

| | | | |
|---|---|---|---|
| C2-N1-C3-C4 | 153.9(8) | C22-C16-C17-O5 | -41.0(4) |
| C1-N1-C3-C4 | -73.5(10) | C15-C16-C17-O5 | 85.1(4) |
| N1-C3-C4-O1 | -172.1(6) | C22-C16-C17-C21 | 28.9(5) |
| C3-C4-O1-C5 | -164.0(5) | C15-C16-C17-C21 | 155.0(3) |
| C4-O1-C5-C10 | 6.2(8) | C22-C16-C17-C18 | -176.4(3) |
| C4-O1-C5-C6 | -173.7(5) | C15-C16-C17-C18 | -50.3(4) |
| O1-C5-C6-C7 | -180.0(4) | C18-C17-O5-C21 | -109.2(4) |
| C10-C5-C6-C7 | 0.1(7) | C16-C17-O5-C21 | 115.2(4) |
| C5-C6-C7-C8 | -1.4(6) | O5-C17-C18-C19 | -84.1(4) |
| C6-C7-C8-C9 | 2.5(6) | C21-C17-C18-C19 | -151.2(4) |
| C6-C7-C8-C11 | -175.9(4) | C16-C17-C18-C19 | 52.5(5) |
| C7-C8-C9-C10 | -2.4(6) | C17-C18-C19-C14 | -55.6(4) |
| C11-C8-C9-C10 | 176.1(4) | O3-C14-C19-C18 | -58.4(4) |
| O1-C5-C10-C9 | -179.9(4) | C15-C14-C19-C18 | 58.6(4) |
| C6-C5-C10-C9 | 0.0(7) | C18-C17-C21-O5 | 102.9(4) |
| C8-C9-C10-C5 | 1.1(6) | C16-C17-C21-O5 | -103.2(4) |
| C9-C8-C11-C12 | -174.7(4) | C17-C16-C22-O6 | -140.9(3) |
| C7-C8-C11-C12 | 3.7(7) | C15-C16-C22-O6 | 93.7(4) |
| C8-C11-C12-C13 | 176.8(4) | C17-C16-C22-C24 | -75.6(4) |
| C11-C12-C13-O2 | 5.8(8) | C15-C16-C22-C24 | 159.0(3) |
| C11-C12-C13-O3 | -173.0(4) | C17-C16-C22-C23 | 83.6(4) |
| O2-C13-O3-C14 | -6.3(7) | C15-C16-C22-C23 | -41.8(4) |
| C12-C13-O3-C14 | 172.5(4) | C23-C22-O6-C24 | -113.1(3) |
| C13-O3-C14-C19 | -82.9(4) | C16-C22-O6-C24 | 110.0(3) |
| C13-O3-C14-C15 | 157.7(4) | C22-O6-C24-C25 | 115.3(4) |
| O3-C14-C15-O4 | -60.5(4) | C23-C22-C24-O6 | 100.9(4) |
| C19-C14-C15-O4 | -179.4(3) | C16-C22-C24-O6 | -100.8(3) |
| O3-C14-C15-C16 | 60.6(4) | O6-C22-C24-C25 | -105.2(4) |
| C19-C14-C15-C16 | -58.3(4) | C23-C22-C24-C25 | -4.3(6) |
| C14-C15-O4-C20 | -76.2(4) | C16-C22-C24-C25 | 153.9(4) |
| C16-C15-O4-C20 | 160.2(3) | O6-C24-C25-C26 | -155.3(3) |
| O4-C15-C16-C17 | 176.9(3) | C22-C24-C25-C26 | -84.1(5) |
| C14-C15-C16-C17 | 53.0(4) | C24-C25-C26-C27 | -101.4(5) |
| O4-C15-C16-C22 | -55.0(4) | C25-C26-C27-C29 | 178.9(4) |
| C14-C15-C16-C22 | -178.8(3) | C25-C26-C27-C28 | -3.3(6) |

Form C

CRYSTALLINE SOLIDS OF A METAP-2 INHIBITOR AND METHODS OF MAKING AND USING SAME

CROSS REFERENCE TO RELATED APPLICATIONS

This application is a continuation of U.S. patent application Ser. No. 14/178,788, filed Feb. 12, 2014, which is a continuation of U.S. patent application Ser. No. 13/679,310, filed Nov. 16, 2012, which is a continuation of U.S. patent application Ser. No. 13/568,476, filed Aug. 7, 2012, which is a continuation of PCT/US2011/059966, filed Nov. 9, 2011, which claims the benefit of and priority to U.S. Provisional Patent Application No. 61/411,655, filed Nov. 9, 2010, all of which is hereby incorporated by reference in their entirety.

BACKGROUND

MetAP2 encodes a protein that functions at least in part by enzymatically removing the amino terminal methionine residue from certain newly translated proteins, such as, glyceraldehyde-3-phosphate dehydrogenase (Warder et al. (2008) *J Proteome Res* 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) *Cancer Res* 63:7861) and infectious diseases, such as, microsporidiosis, leishmaniasis, and malaria (Zhang et al. (2002) *J. Biomed Sci.* 9:34). Notably, inhibition of MetAP2 activity in obese and obese-diabetic animals leads to a reduction in body weight in part by increasing the oxidation of fat and in part by reducing the consumption of food (Rupnick et al. (2002) *Proc Natl Acad Sci USA* 99:10730).

6-O-(4-Dimethylaminoethoxy)cinnamoyl fumagillol is a METAP2 inhibitor and is useful in the treatment of, e.g., obesity. 6-O-(4-Dimethylaminoethoxy)cinnamoyl fumagillol is characterized by formula I:

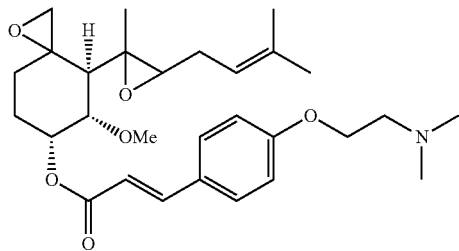 [SMILES: CO[C@@H]1[C@H](OC(=O)/C=C/c2ccc(OCCN(C)C)cc2)CCC2(CO2)[C@H]1C1(C)OC1CC=C(C)C]

An amorphous form of a hemioxalate salt of 6-O-(4-dimethylaminoethoxy)cinnamoyl fumagillol has been prepared. However, the existence or preparation of a crystalline form of the free base of 6-O-(4-Dimethylaminoethoxy) cinnamoyl fumagillol does not appear to be disclosed in the art.

Polymorphism is the ability of a substance to crystallize in more than one crystal lattice arrangement. Crystallization, or polymorphism, can influence many aspects of solid state properties of a drug substance. A crystalline substance may differ considerably from an amorphous form, and different crystal modifications of a substance may differ considerably from one another in many respects including solubility, dissolution rate and/or bioavailability. Generally, it is difficult to predict whether or not a given compound will form various crystalline solid state forms. It is even more difficult to predict the physical properties of these crystalline solid state forms. Further, it can be advantageous to have a crystalline form of a therapeutic agent for certain formulations, e.g., formulations suitable for subcutaneous use.

SUMMARY

In an embodiment, provided herein is a composition comprising a crystalline form of 6-O-(4-dimethylaminoethoxy)cinnamoyl fumagillol. A crystalline form of 6-O-(4-dimethylaminoethoxy)cinnamoyl fumagillol, free base, is also provided herein, characterized by a powder X-ray diffraction pattern having a characteristic peak in degrees 2θ at about 13.3, or for example, characterized by a powder X-ray diffraction pattern having characteristic peaks in degrees 2θ at 13.3, 17.4, and 19.9, or for example, characterized by a powder X-ray diffraction pattern having characteristic peaks in degrees 2θ at 7.1, 13.3, 16.3, 17.4, 18.6, 19.4, and 19.9, or for example, characterized by a powder X-ray diffraction pattern having characteristic peaks in degrees 2θ at 5.2, 7.1, 10.4, 13.3, 14.2, 16.3, 17.4, 18.6, 19.4, and 19.9, e.g., characterized by the crystallization pattern shown in FIG. 1. In some embodiments, the powder X-ray diffraction pattern may be obtained using Cu Kα radiation.

Also provided herein is a crystalline form of 6-O-(4-dimethylaminoethoxy)cinnamoyl fumagillol, free base, having a space group of $P2_12_12_1$.

In one embodiment, the crystalline form of 6-O-(4-dimethylaminoethoxy)cinnamoyl fumagillol, free base, in solution may have a $^1H$ NMR spectrum substantially in accordance with the pattern shown in FIG. 6.

Also provided herein is a process for preparing a crystalline form of 6-O-(4-dimethylaminoethoxy)cinnamoyl fumagillol, (e.g., form A) comprising:

a) preparing a solution of 6-O-(4-dimethylaminoethoxy) cinnamoyl fumagillol, e.g., amorphous 6-O-(4-dimethylaminoethoxy)cinnamoyl fumagillol, in a solvent. For example, a solvent may be a secondary ether, e.g., diisopropyl ether, or maybe e.g., a solvent/antisolvent system, e.g., a toluene:n-heptane mixture, e.g., with a ratio of n-heptane to toluene of about 4:1;

b) heating the solution, e.g., to about 40° C. to about 60° C., e.g., to about 50° C., to substantially or completely dissolve the 6-O-(4-dimethylaminoethoxy)cinnamoyl fumagillol;

c) adjusting the temperature so that solid precipitates out of the solution; and d) isolating the crystalline form of 6-O-(4-dimethylaminoethoxy)cinnamoyl fumagillol.

Such a process that includes adjusting temperature may comprise cooling the solution to about 4° C. or less, or to about 2° C. to about 10° C.

A pharmaceutical composition comprising the crystalline form provided herein and a pharmaceutically acceptable excipient is contemplated, for example, a composition that is a suspension formulation suitable for subcutaneous injection. Provided herein, in an embodiment, is a drug substance comprising at least a detectable amount of the provided crystalline form.

A method of treating obesity in a patient in need thereof is also provided that includes administering to the patient an effective amount of a crystalline form provided herein. Also provided herein is a method of treating obesity in patient in need thereof, comprising subcutaneously administering a composition comprising a crystalline form of 6-O-(4-dimethylaminoethoxy)cinnamoyl fumagillol (free base).

Still another aspect of the invention provides a kit comprising a disclosed a crystalline form.

DETAILED DESCRIPTION

Figure 1:
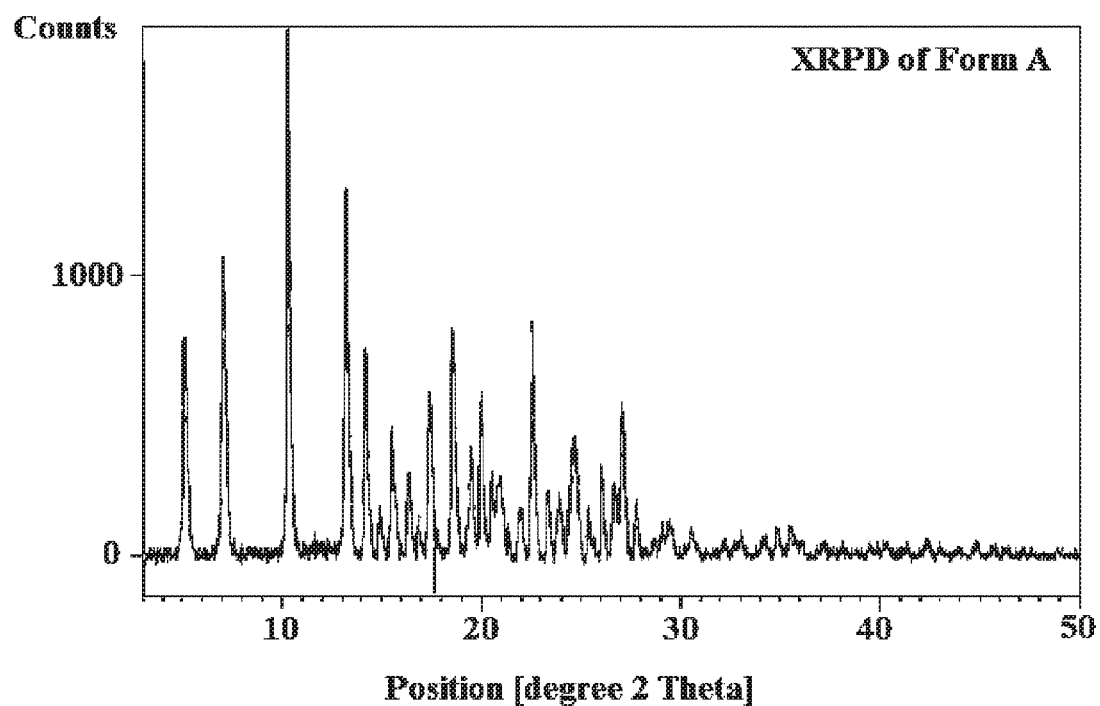
FIG. 1 depicts the X-ray diffraction pattern of Form A.

At least in part, this disclosure is directed to crystalline forms of 6-O-(4-dimethylaminoethoxy)cinnamoyl fumagillol (free base). The disclosure also provides for a pharmaceutical composition comprising crystalline 6-O-(4-dimethylaminoethoxy)cinnamoyl fumagillol (free base) and a pharmaceutically acceptable carrier. The term "crystalline form" refers to a crystal form or modification that can be characterized by analytical methods such as, e.g., X-ray powder diffraction or Raman spectroscopy. For example, provided herein is a drug substance comprising at least a detectable amount of a disclosed crystalline form of 6-O-(4-dimethylaminoethoxy)cinnamoyl fumagillol.

Provided herein is a crystalline form of 6-O-(4-dimethylaminoethoxy)cinnamoyl fumagillol, free base, characterized by a powder X-ray diffraction pattern having a characteristic peak in degrees 2θ at about 13.3 (referred to herein as "Form A"). In one embodiment, the crystalline form of 6-O-(4-dimethylaminoethoxy)cinnamoyl fumagillol (free base) is characterized by a powder X-ray diffraction pattern that has a characteristic peak in degrees 2θ at about 5.2, or is characterized by a powder X-ray diffraction pattern that has a characteristic peak in degrees 2θ at about 7.1, or is characterized by a powder X-ray diffraction pattern that has a characteristic peak in degrees 2θ at about 10.4, or is characterized by a powder X-ray diffraction pattern that has a characteristic peak in degrees 2θ at about 14.2, or is characterized by a powder X-ray diffraction pattern that has a characteristic peak in degrees 2θ at about 15.5, or is characterized by a powder X-ray diffraction pattern that has a characteristic peak in degrees 2θ at about 16.3, or is characterized by a powder X-ray diffraction pattern that has a characteristic peak in degrees 2θ at about 17.4, or is characterized by a powder X-ray diffraction pattern that has a characteristic peak in degrees 2θ at about 18.6, or is characterized by a powder X-ray diffraction pattern that has a characteristic peak in degrees 2θ at about 19.4, or is characterized by a powder X-ray diffraction pattern that has a characteristic peak in degrees 2θ at about 19.9, or is characterized by a powder X-ray diffraction pattern that has a characteristic peak in degrees 2θ at about 20.9, or is characterized by a powder X-ray diffraction pattern that has a characteristic peak in degrees 2θ at about 22.6, or is characterized by a powder X-ray diffraction pattern that has a characteristic peak in degrees 2θ at about 24.6. In another embodiment, the crystalline form is characterized by a powder X-ray diffraction pattern having at least one or more characteristic peaks in degrees 2θ at about 13.3, 17.4, and 19.9. In a further embodiment, the crystalline form is characterized by a powder X-ray diffraction pattern having at least one or more characteristic peaks in degrees 2θ at about 7.1, 13.3, 16.3, 17.4, 18.6, 19.4, and 19.9. In yet another embodiment, the crystalline form is characterized by a powder X-ray diffraction pattern having at least one or more characteristic peaks in degrees 2θ at about 5.2, 7.1, 10.4, 13.3, 14.2, 16.3, 17.4, 18.6, 19.4, and 19.9. In some embodiments, the crystalline form is characterized by a powder X-ray diffraction pattern having at least one or more characteristic peaks in degrees 2θ at about 5.2, 7.1, 10.4, 13.3, 14.2, 15.5, 16.3, 17.4, 18.6, 19.4, 19.9, 20.9, 22.6, and 24.6. The term "about" in this context means that there is an uncertainty in the measurements of the 2θ of ±0.5 (expressed in 2θ) or that there is an uncertainty in the measurements of the 2θ of ±0.2 (expressed in 2θ). For example, a contemplated crystalline form has a powder X-ray diffraction pattern shown in FIG. 1. In one embodiment, the powder X-ray diffraction pattern of the crystalline form was obtained using Cu Kα radiation. In a further example, a contemplated crystalline form has a $^1$H NMR spectrum substantially in accordance with the pattern shown in FIG. 6, wherein the crystalline form is in solution.

Also provided herein is a crystalline form of 6-O-(4-dimethylaminoethoxy)cinnamoyl fumagillol, free base, having a space group of $P2_12_12_1$.

The crystalline form of Form A 6-O-(4-dimethylaminoethoxy)cinnamoyl fumagillol has an IR absorption spectrum having at least one or more characteristic peaks at about 2971, 2938, 2817, 2762, 1163, 1103, 832 cm$^{-1}$. In this context, the term "about" means that the cm$^{-1}$ values can vary, e.g., up to ±5 cm$^{-1}$. A contemplated crystalline form is characterized by the IR absorption spectrum shown in FIG. 5. The contemplated crystalline form of 6-O-(4-dimethylaminoethoxy)cinnamoyl fumagillol may be characterized by a melting point of about 83° C., for example, and may be characterized by a differential scanning calorimetry profile with an endotherm at about 83.1° C. Form A, for example, has a solubility in diisopropyl ether of about 25 mg/mL at room temperature (ca. 20° C.) and about 102 mg/mL at 50° C. The solubility of Form A in solvent (e.g., an aqueous solution that may include a buffer) with a pH greater or equal to about 8.0 may be less than about 0.2 mg/mL at ca. 20° C. Contemplated crystalline forms disclosed herein may be substantially more stable as compared, for example, to amorphous free base and/or amorphous hemioxalate salt of 6-O-(4-dimethylaminoethoxy)cinnamoyl fumagillol.

Also provided herein is a process for preparing a crystalline form 6-O-(4-dimethylaminoethoxy)cinnamoyl fumagillol (free base), e.g., Form A, comprising:

a) preparing a solution of 6-O-(4-dimethylaminoethoxy) cinnamoyl fumagillol, e.g., amorphous 6-O-(4-dimethylaminoethoxy)cinnamoyl fumagillol in a solvent.

Such solvents contemplated may include e.g., a secondary ether, toluene, n-heptane, or a combination of two or more solvents, and/or a solvent/anti-solvent system;

b) heating the solution to completely dissolve the 6-O-(4-dimethylaminoethoxy)cinnamoyl fumagillol;

c) adjusting the temperature so that solid precipitates out of the solution; and d) isolating the crystalline form of 6-O-(4-dimethylaminoethoxy)cinnamoyl fumagillol.

In an exemplary embodiment, the secondary ether is diisopropyl ether. Other contemplated solvents include alcohols such as methanol and/or isopropanol, and solvents such as acetone, acetonitrile, cyclohexane, ethyl acetate, n-heptane, methyl ethyl ketone, methyl isobutyl ketone, tetrahydrofuran, toluene, and/or a combination of two or more thereof. For example, in one embodiment the solvent may be a toluene:n-heptane mixture, wherein the ratio of n-heptane to toluene is, for example, about 10:1, about 9:1, about 8:1, about 7:1, about 6:1, about 5:1, about 4:1, about 3:1, about 2:1, or about 1:1. In another example, the solvent or solvent/anti-solvent system is selected from ethyl acetate:n-heptane; acetone:n-heptane; or methyl ethyl ketone:n-heptane. Contemplated ratios of antisolvent to solvent include, for example, about 15:1, about 14:1, about 13:1, about 12:1, about 11:1, about 10:1, about 9:1, about 8:1, about 7:1, about 6:1, about 5:1, about 4:1, about 3:1, about 2:1, or about 1:1. In some embodiments, heating the solution comprises heating the solution to about 40° C. to about 60° C., e.g., to about 50° C. In another embodiment, adjusting the temperature comprises cooling the solution to about 0° C. to about 10° C., e.g., to about 4° C. In one embodiment, adjusting temperature comprises cooling the solution to about 4° C. or less, or to about 2° C. to about 10° C. Such systems may be used with or without seeding. For example, contemplated processes may also include incorporating or seeding a solution with an existing crystal of 6-O-(4-dimethylaminoethoxy)cinnamoyl fumagillol.

In another embodiment, a different crystalline form of 6-O-(4-dimethylaminoethoxy)cinnamoyl fumagillol (free base), characterized by a powder X-ray diffraction pattern having characteristic peaks in degrees 2θ at one or more of positions at about 6.1 and 18.4 or at about 6.1, 12.2, 12.8, 12.9, 18.4, 18.6, 19.7, 20.2, 24.1, and 24.7. (referred to herein as "Form C"), is provided. The term "about" in this context means for example, that there is an uncertainty in the measurements of the 2θ of ±0.5 (expressed in 2θ) or even that there is an uncertainty in the measurements of the 2θ of ±0.2 (expressed in 2θ). For example, a contemplated crystalline form has a powder X-ray diffraction pattern shown in FIG. 14.

Form C of 6-O-(4-dimethylaminoethoxy)cinnamoyl fumagillol has an IR absorption spectrum having characteristic peaks at about at least one of: 831, 894, 1106, 1159, 1249, 1287, 1512, 1602, 1631, and 1707 $cm^{-1}$. In this context, the term "about" means that the $cm^{-1}$ values can vary, e.g. up to ±5 $cm^{-1}$. For example, a contemplated crystalline form is characterized by the IR absorption spectrum shown in FIG. 15. The contemplated crystalline Form C of 6-O-(4-dimethylaminoethoxy)cinnamoyl fumagillol exhibits plate-like morphology. In one embodiment, Form C converts or reverts to Form A after, for example, about three days of storage at either 5° C. or ambient temperature.

Methods

In certain embodiments, the disclosure provides a method of treating and or ameliorating obesity in a patient in need thereof by administering an effective amount of a disclosed crystalline compound, e.g., Form A. Also provided herein are methods for inducing weight loss in a patient in need thereof, comprising administering a disclosed crystalline compound.

Other contemplated methods of treatment include methods of treating or amelioriating an obesity-related condition or co-morbidity, by administering a crystalline compound disclosed herein to a subject. For example, contemplated herein are methods for treating type 2 diabetes in a patient in need thereof and/or method of treating a patient suffering from diabetes, for other contemplated diseases or disorders Exemplary co-morbidities or other disorders that may be treated by a disclosed compound may include cardiac disorders, endocrine disorders, respiratory disorders, hepatic disorders, skeletal disorders, psychiatric disorders, metabolic disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

In particular, in certain embodiments, the disclosure provides a method of treating the above medical indications comprising administering to a subject in need thereof a therapeutically effective amount of a compound described herein. In certain other embodiments, a method of treating obesity in patient in need thereof is provided, comprising subcutaneously administering a composition comprising a crystalline form of 6-O-(4-dimethylaminoethoxy)cinnamoyl fumagillol.

Obesity or reference to "overweight" refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight (kg)/height$^2$ (m$^2$) (SI) or 703×weight (lb)/height$^2$ (in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered "obese" at a level differing from the general guidelines described above.

The crystalline compounds disclosed herein can be used as a medicament or pharmaceutically acceptable composition, e.g., in the form of pharmaceutical preparations for entereal, parenteral, or topical administration, and the contemplated methods disclosed herein may include administering enterally, parenterally, or topically a disclosed crystalline compound, or a composition comprising or formed from such a disclosed crystalline compounds. For example, the disclosed crystalline Form A may be capable of controlling one or more pharmacokinetic properties (e.g., a longer or shorter release profile) when administered by a certain route (e.g., subcutaneous) or in a certain formulation, as compared to a different route (e.g., intravenous) or other formulation e.g., a formulation having the amorphous form. In one embodiment, a disclosed crystalline form, e.g., Form A, may afford substantial reproducibility from one formulation to another.

Compositions

Another aspect of the disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, ocular, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants. For example, crystalline forms provided herein may be milled to obtain a particular particle size, and in at least some embodiments, such crystalline forms may remain substantially stable upon milling.

For example, provided herein is a composition suitable for subcutaneous administration, comprising a suspension of the disclosed crystalline form. Subcutaneous administration can be advantageous over intravenous administration, which typically requires a doctor visit, and can be more painful and invasive. A typical dose of the crystalline compound, when administered to a patient, may be about 1 mg to about 8 mg of compound. In an embodiment, disclosed herein is a pharmaceutically acceptable composition formed from a disclosed crystalline form, e.g. by mixing a crystalline form with an excipient and/or a solvent.

Kits

In one embodiment, a kit for treating obesity or other contemplated disorder is provided. For example, a disclosed kit comprises a disclosed crystalline compound, e.g. a crystalline form of 6-O-(4-dimethylaminoethoxy)cinnamoyl fumagillol, free base, e.g., Form A, for example, disposed in an e.g. first container. In some embodiments, a kit may further include a pharmaceutically acceptable excipient, disposed in e.g. a second container. Such contemplated kits may include written instructions describing preparation of a pharmaceutical composition suitable for administration to a patient from the crystalline form. For example, the written instructions may describe preparing a pharmaceutically acceptable form for patient administration by e.g. mixing an excipient and a crystalline compound disclosed herein. Disclosed kits may further comprise written instructions describing how to administer the resulting composition to the patient.

EXAMPLES

The compounds described herein can be prepared in a number of ways based on the teachings contained herein and synthetic procedures known in the art. The following non-limiting examples illustrate the disclosed inventions.

Example 1

Crystalline, Form A material of 6-O-(4-dimethylaminoethoxy)cinnamoyl fumagillol was prepared as follows:

Approximately 423 mg of amorphous gum/oil-like 6-O-(4-dimethylaminoethoxy)cinnamoyl fumagillol free base compound was dissolved in ca. 6 mL of diisopropylether (IPE). The solution was allowed to stir for ca. 24 hours at ambient temperature (18-22° C.) during which time solid precipitated. The resulting solid was isolated by filtration and dried under vacuum at ambient for ca. 4 hours (yield 35.8%).

X-ray powder diffraction (XRPD) analysis was conducted on the solid crystals (Form A). XRPD analysis was carried out on a Siemens D5000, scanning the samples between 3 and 30 or 50° 2θ. For samples <100 mg, ca. 5 mg of sample was gently compressed onto a glass substrate which was inserted into a plastic sample holder. For samples >100 mg, ca. 100 mg of sample was gently compressed into a plastic sample holder, so that the sample surface was smooth and just above the level of the sample holder. The sample was then loaded into the diffractometer running in reflection mode and analyzed, using the following experimental conditions, seen in Table 1 below.

TABLE 1

| | |
|---|---|
| Start Position [°2Th.] | 3.0000 |
| End Position [°2Th.] | 30.000 or 50.000 |
| Step Size [°2Th.] | 0.0200 |
| Scan Step Time [s] | 0.8 |
| Scan Type | Continuous |
| Offset [°2Th.] | 0.0000 |
| Divergence Slit Type | Fixed |
| Divergence Slit Size [°] | 2.0000 |
| Specimen Length [mm] | various |
| Receiving Slit Size [mm] | 0.2000 |
| Measurement Temperature [° C.] | 20.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 (nominal) |

TABLE 1-continued

| | |
|---|---|
| Generator Settings | 40 mA, 40 kV |
| Diffractometer Type | D5000 |
| Diffractometer Number | 0 |
| Goniometer Radius [mm] | 217.50 |
| Incident Beam Monochromator | No |
| Diffracted Beam Monochromator | (Graphite) |
| Spinning | No |

Raw Data Origin Siemens-binary V2 (.RAW)

The XRPD is shown in FIG. 1. Characteristic peaks include one or more of the peaks shown in Table 2, below.

TABLE 2

| Pos. [°2Th.] | Height [cts] | d-spacing [Å] | Rel. Int. [%] |
|---|---|---|---|
| 5.2216 | 879.97 | 16.92464 | 38.74 |
| 7.1328 | 1614.46 | 12.39351 | 71.08 |
| 8.4170 | 68.52 | 10.50516 | 3.02 |
| 10.3980 | 1371.44 | 8.50784 | 60.38 |
| 13.2602 | 2271.45 | 6.67717 | 100.00 |
| 14.2394 | 1328.46 | 6.22010 | 58.49 |
| 14.9084 | 906.94 | 5.94247 | 39.93 |
| 15.5184 | 1004.89 | 5.71023 | 44.24 |
| 15.7074 | 710.54 | 5.64192 | 31.28 |
| 16.3212 | 1491.01 | 5.43113 | 65.64 |
| 17.4000 | 2139.83 | 5.09673 | 94.21 |
| 18.6247 | 1628.64 | 4.76426 | 71.70 |
| 19.4797 | 1454.94 | 4.55704 | 64.05 |
| 19.9991 | 1691.63 | 4.43986 | 74.47 |
| 20.5602 | 710.33 | 4.31993 | 31.27 |
| 20.8627 | 1054.54 | 4.25797 | 46.43 |
| 21.0382 | 624.42 | 4.22285 | 27.49 |
| 21.9610 | 557.90 | 4.04744 | 24.56 |
| 22.6008 | 1083.17 | 3.93430 | 47.69 |
| 23.3508 | 755.63 | 3.80961 | 33.27 |
| 23.9357 | 559.19 | 3.71782 | 24.62 |
| 24.5704 | 1098.96 | 3.62320 | 48.38 |
| 25.4387 | 240.68 | 3.50146 | 10.60 |
| 26.1594 | 243.27 | 3.40661 | 10.71 |
| 26.6610 | 598.48 | 3.34364 | 26.35 |
| 27.0969 | 679.42 | 3.28812 | 29.91 |
| 27.1788 | 612.15 | 3.28111 | 26.95 |
| 27.7736 | 401.98 | 3.21218 | 17.70 |
| 28.6369 | 293.31 | 3.11728 | 12.91 |
| 29.0724 | 260.75 | 3.07156 | 11.48 |
| 29.3437 | 171.15 | 3.04378 | 7.54 |
| 30.5513 | 193.45 | 2.92617 | 8.52 |
| 32.1240 | 73.64 | 2.78641 | 3.24 |
| 32.9570 | 111.68 | 2.71787 | 4.92 |
| 34.1346 | 107.25 | 2.62675 | 4.72 |
| 34.8872 | 145.93 | 2.57179 | 6.42 |
| 35.5321 | 180.47 | 2.52657 | 7.95 |
| 37.1636 | 88.30 | 2.41932 | 3.89 |
| 38.0368 | 45.49 | 2.36577 | 2.00 |
| 39.4407 | 74.74 | 2.28473 | 3.29 |
| 40.2350 | 76.46 | 2.24145 | 3.37 |
| 41.1595 | 53.90 | 2.19321 | 2.37 |

Figure 2:
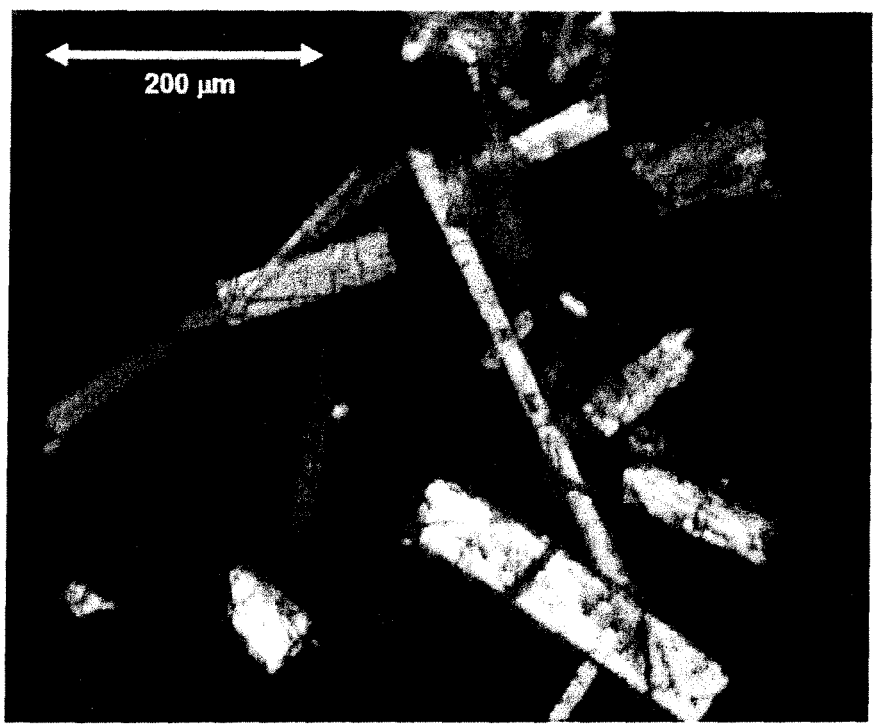
FIG. 2 is a micrograph of Form A.

The presence of birefringence was determined by polarized light microscopy (PLM) using an Olympus BX50F4 polarising microscope, equipped with a Motic camera and image capture software (Motic Images Plus 2.0). Images were recorded using 20× objective. Approximately, 1 mg of sample was placed onto a microscope slide in each case, as shown in FIG. 2.

Figure 3:
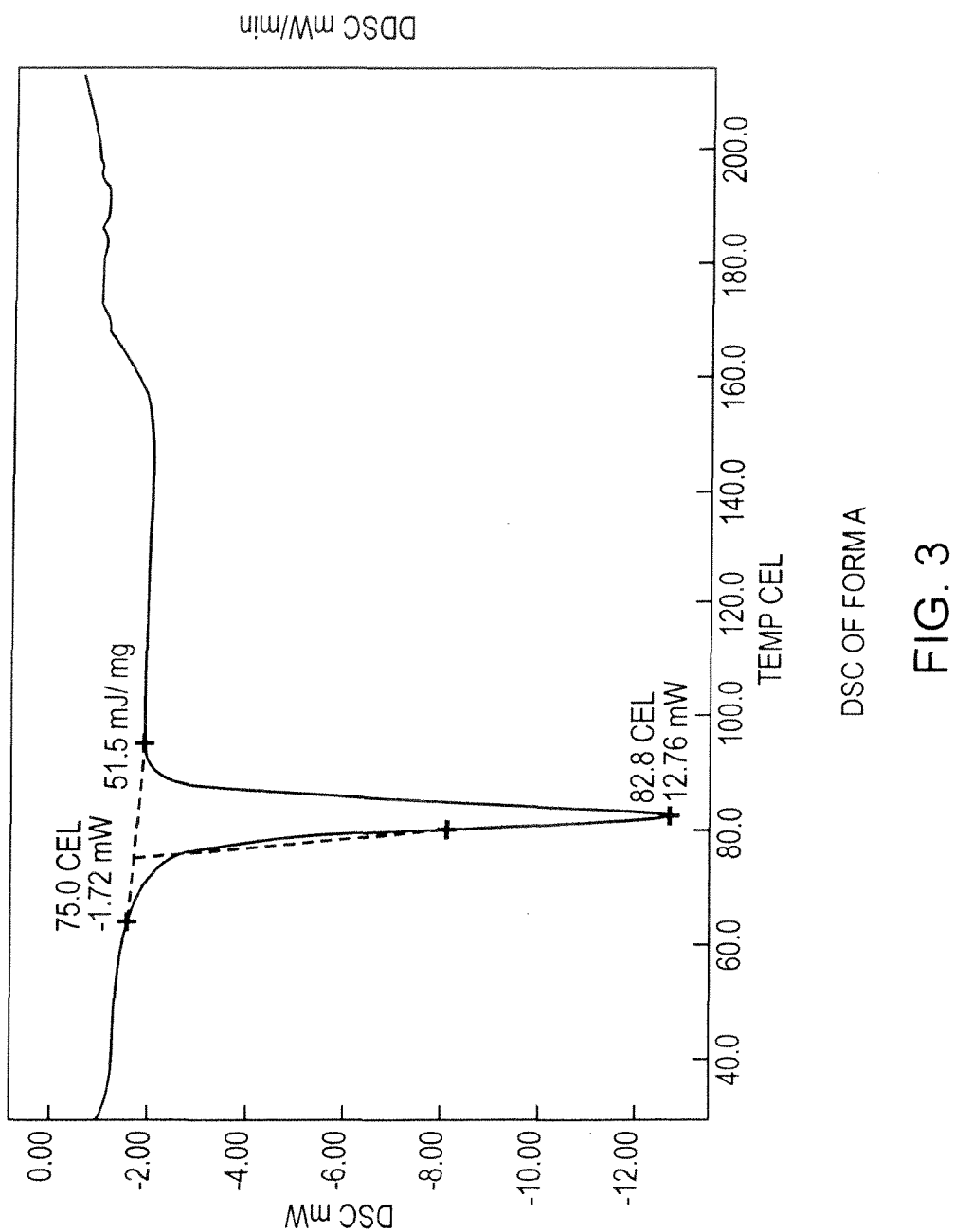
FIG. 3 depicts the characterization of Form A by differential scanning calorimetry (DSC).

The crystalline compound was also characterized by differential scanning calorimetry. Approximately 5-10 mg of sample was weighed into an aluminum DSC pan and sealed with a pierced aluminum lid (non-hermetically), unless specified otherwise. The DSC pan was then loaded into a Seiko DSC6200 (equipped with a cooler) cooled and held at 25° C. Once a stable heat-flow response was obtained, the sample and reference were then heated to ca. 280° C. at scan rate of 10° C./min and the resulting heat flow response monitored. Nitrogen was used as the purge gas, at a flow rate of 150 cm³/min. The instrument was temperature and heat-flow calibrated on a weekly basis using an indium reference standard. Sample analysis was carried out using Muse Measurement software (version 5.4 U) where the temperatures of thermal events were quoted as the onset temperature, measured according to the manufacturer's specifications. Results are depicted in FIG. 3. All endotherms present in the DSC traces point in the downward direction.

Figure 4:
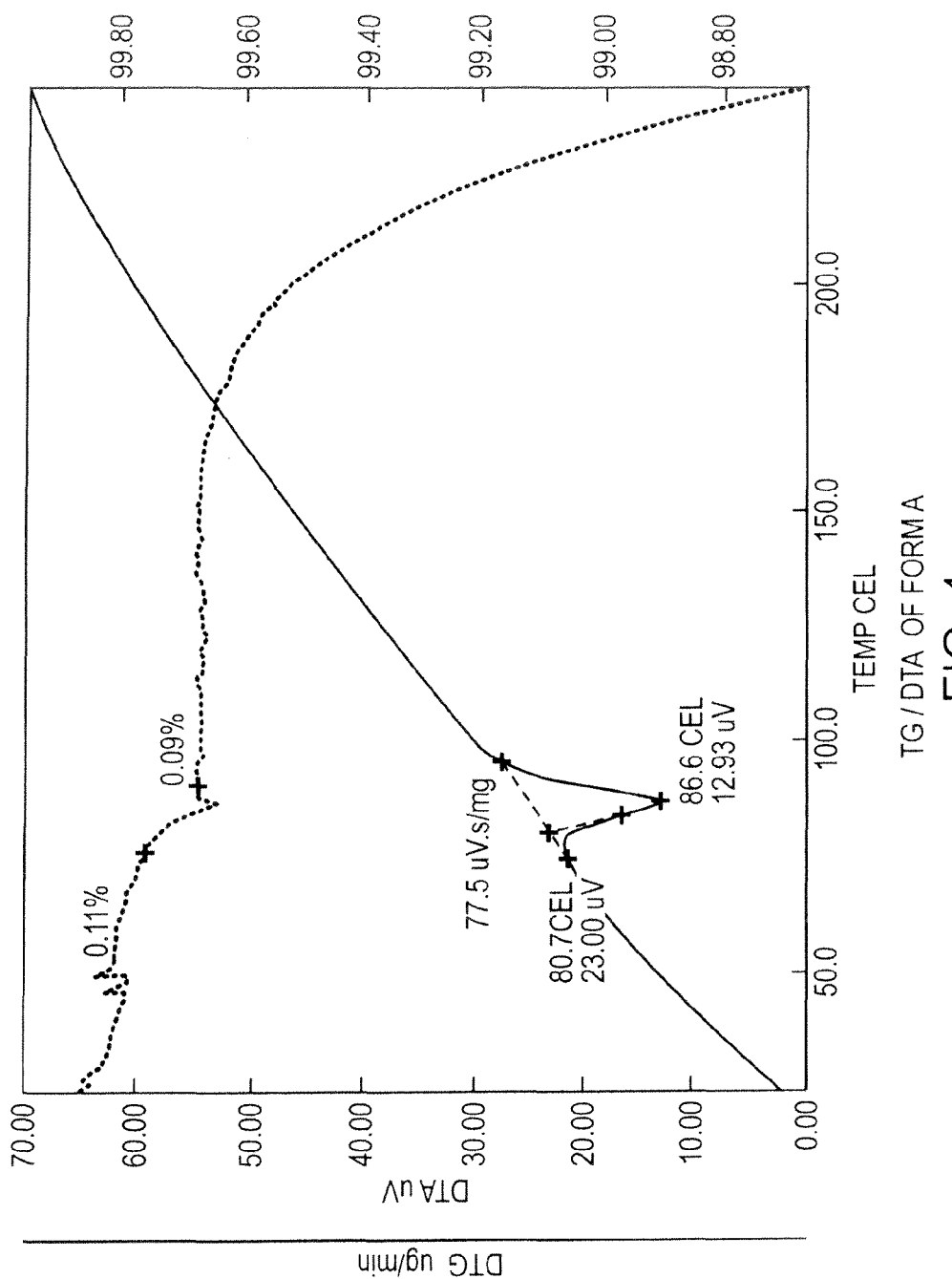
FIG. 4 depicts the characterization of Form A by thermogravimetric/differential thermal analysis (TG/DTA).

Thermogravimetric/Differential Thermal Analysis (TG/DTA) was also conducted. Approximately, 5-10 mg of sample was weighed into an aluminium pan and loaded into a simultaneous thermogravimetric/differential thermal analyser (TG/DTA) held at room temperature. The sample was then heated at a rate of 10° C./min from 25° C. to 280° C. during which time the change in sample weight was recorded along with any differential thermal events (DTA). Nitrogen was used as the purge gas, at a flow rate of 150 cm³/min. The instrument was weight and temperature calibrated on a monthly basis using a 100 mg reference weight and an indium reference standard, respectively. Sample analysis was carried out using Muse Measurement software (version 5.4 U). Results are depicted in FIG. 4.

Figure 5:
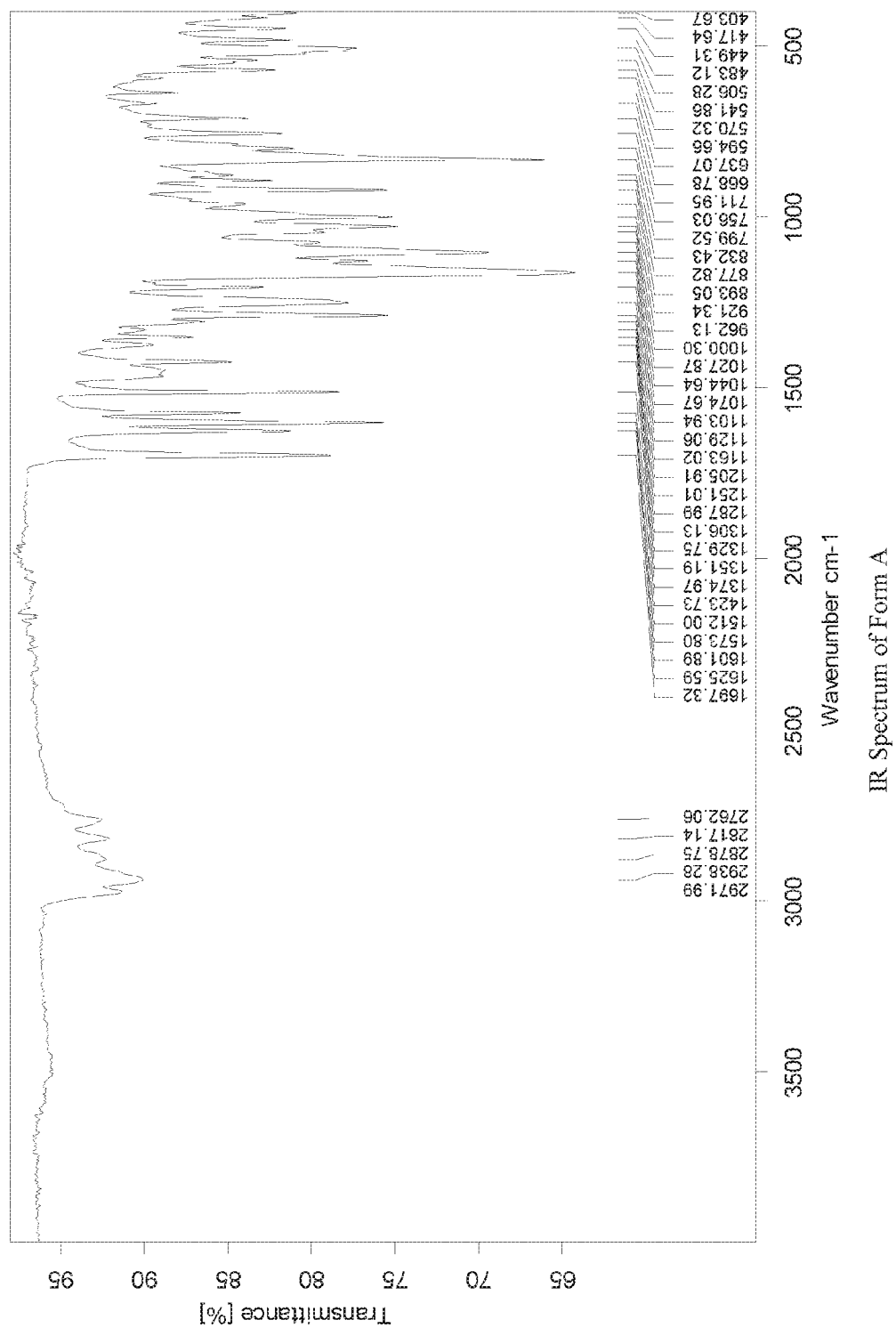
FIG. 5 depicts the FT-IR spectrum of a disclosed crystal form prepared 1 (Form A).

Infra-red spectroscopy was carried out on a Bruker Alpha FT-IR Spectrometer. Approximately, 2-20 mg of material was used for the analysis and samples were either liquid or solid. Spectra were obtained using the following parameters: Resolution: 4 cm$^{-1}$; Background scan time: 16 scans; Sample scan time: 16 scans; Data collection: 4000 to 400 cm$^{-1}$; Result Spectrum: Transmittance; Software: OPUS version 6.5. FIG. 5 depicts the IR spectrum of the prepared crystalline compound.

Figure 6:
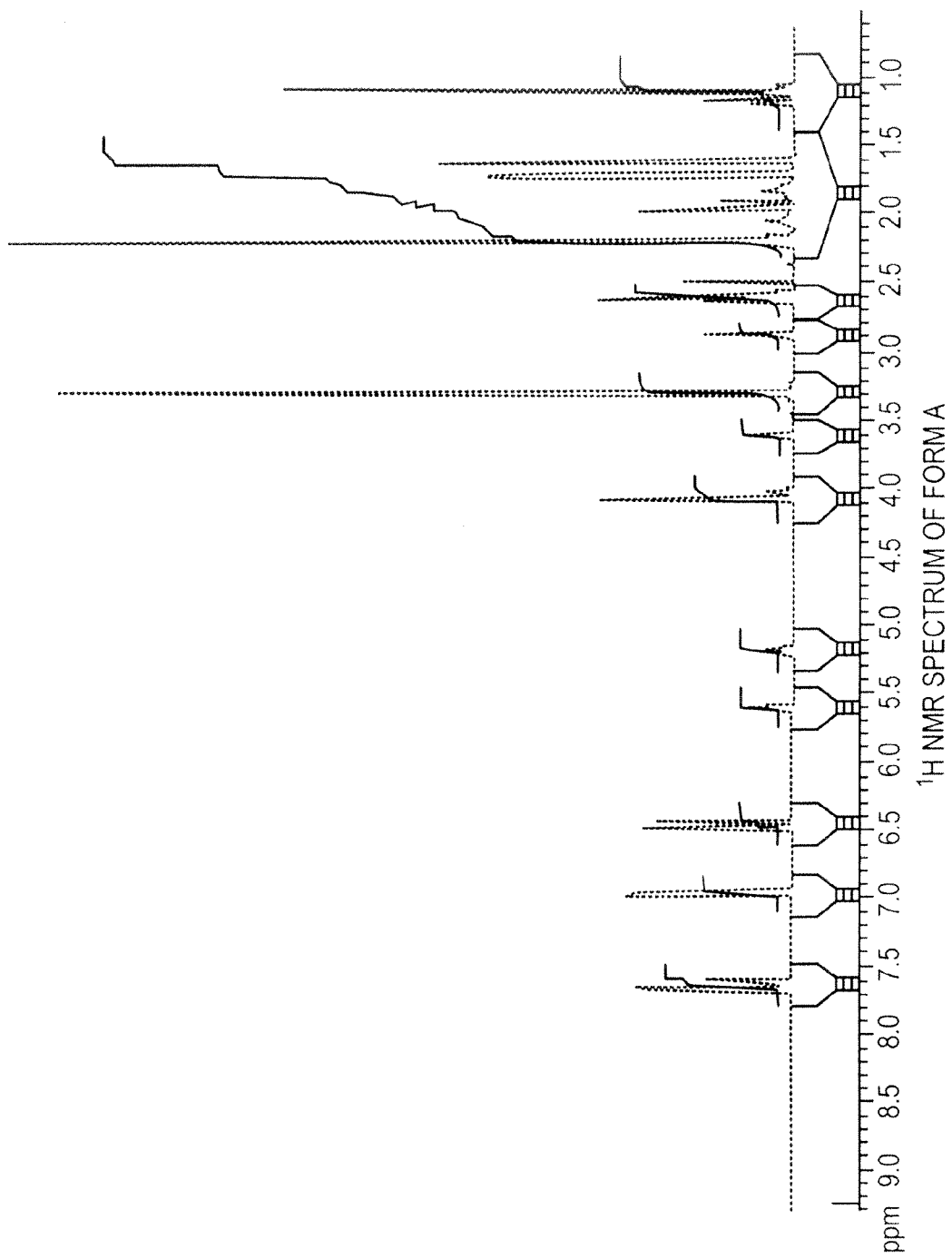
FIG. 6 depicts the NMR spectrum of the dissolved crystal form prepared by Example 1.

$^1$H NMR was performed on a Bruker DPX400 NMR spectrometer. Samples were prepared in deuterated DMSO, and prepared to between 10-20 mg/mL concentration, and the spectrum is depicted in FIG. 6.

Example 2

Crystalline, Form A material of 6-O-(4-dimethylaminoethoxy)cinnamoyl fumagillol (free base) was scaled up as follows:

Diisopropyl ether (90 mL) was added to a round-bottomed flask (250 mL) containing 11.14 g of amorphous gum-/oil-like material. The flask was then heated to 50° C. with a condenser attached to the neck of the flask. This allowed for the amorphous material to dissolve. The solution was stirred at ca. 300 rpm. After remaining at 50° C. for five minutes, the solution was then cooled at a rate of ca. 1° C./minute whilst stirring at ca. 300 rpm. Once the temperature had cooled down to 46° C., 68.2 mg of crystalline material was added to the flask for seeding. After having cooled down to ca. 24° C., solid began to precipitate out of solution and the precipitation continued as the experiment was cooled down to 4° C. After reaching 4° C., it was held at this temperature for ca. 5 minutes. The material was then filtered and allowed to stand on the filter for 5 minutes in order to dry. The material was then transferred to a beaker and placed in a vacuum oven (ca. 600 mbar) at ambient temperature (ca. 20° C.) in order to dry further. After remaining in the vacuum oven for 24 hours, the sample was weighed.

NMR analysis indicated the presence of ca. 2% residual solvent after drying for 24 hours. The sample was therefore dried for a further 24 hours (i.e. 48 hours of drying in total) under vacuum (ca. 600 mbar) at ambient temperature (ca.

Figure 7:
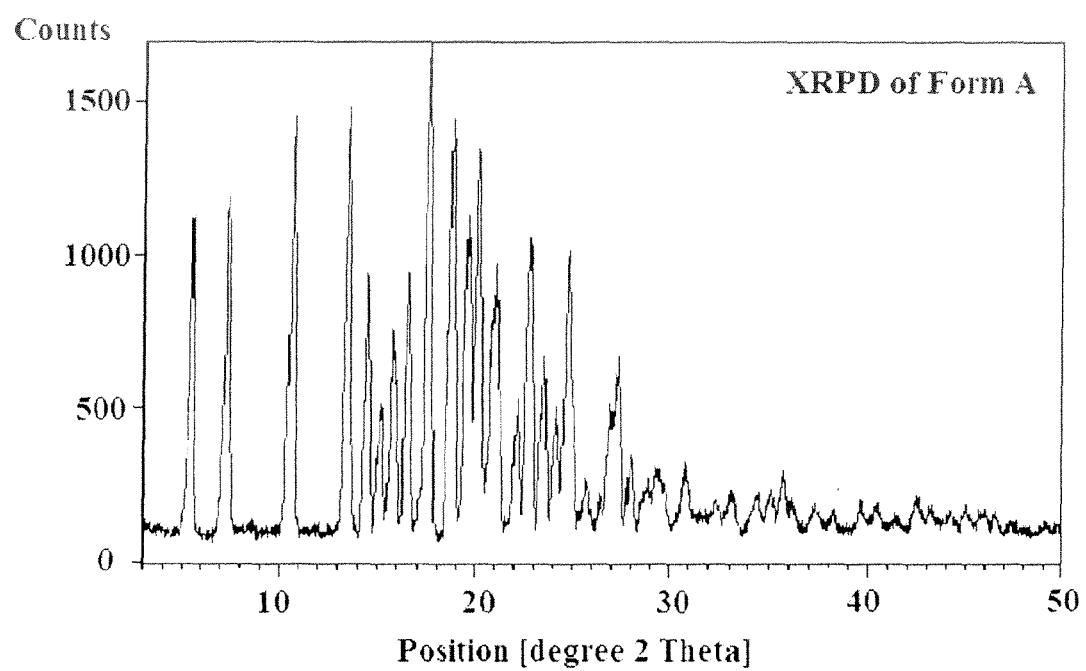
FIG. 7 is a X-ray diffraction pattern of Form A.

20° C.). After the further drying was carried out, no trace of residual solvent could be identified by NMR analysis. The yield was 80%, and HPLC analysis indicated a purity of greater than 99.5%. XPRD is shown in FIG. 7.

Example 3

Figure 8:
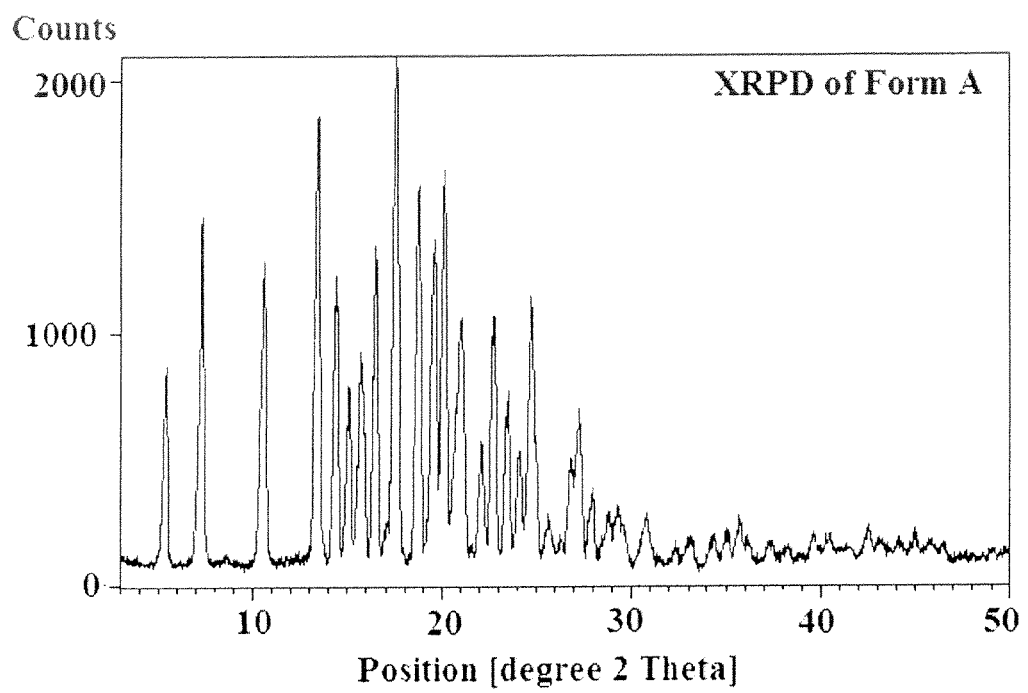
FIG. 8 is a X-ray diffraction pattern of Form A.

The grinding of 500 mg of crystalline, Form A material of 6-O-(4-dimethylaminoethoxy)cinnamoyl fumagillol was done, as follows:

A sample (ca. 500 mg) from the scale-up of crystalline compound as in Example 2 was placed onto a mortar (Agate material, H: 35 mm, L: 77 mm). The sample was then ground using a pestle (length: 80 mm; grinding diameter: 17 mm) for approximately 5 minutes. Throughout the grinding procedure, the sample was allowed to stand for ca. 10 seconds intermittently to ensure that significant heat was not generated. PLM indicated birefrigent material with particle sizes measuring between about 20 μm and 80 μm in length. XRPD analysis indicated that the material remained highly crystalline with peak positions consistent with the un-ground crystalline material (FIG. 8).

Example 4

Crystalline, Form A material of 6-O-(4-dimethylaminoethoxy)cinnamoyl fumagillol (free base) was scaled up as follows:

A 20 mL round-bottom flask was equipped with a stir bar or mechanical stirrer and a reflux condenser (it is not needed to have the condenser connected to cold water supply; air cooling is typically enough for the crystallization purpose). In a separate small vial, 6-O-(4-dimethylaminoethoxy)cinnamoyl fumagillol (1 g) was dissolved in ethyl acetate (1 mL). The resulting solution was filtered through a PTFE 0.2 um filter into the aforementioned 20 mL round bottomed flask using nitrogen pressure. The vial was washed with ethyl acetate (0.25 mL), and the resulting solution was filtered through the same PTFE 0.2 um filter using nitrogen pressure into the flask containing the filtrate. n-Heptane (10 mL) was filtered through the same PTFE 0.2 um filter using nitrogen pressure into the flask containing the filtrate (Note: significant precipitation is observed during the addition of n-heptane to the ethyl acetate solution). The resulting mixture was slowly heated to about 50-55° C. (Note: complete dissolution is often seen between 35-40° C.). The solution was slowly cooled to 35° C., at which point stirring is stopped and seed crystals (1 mg, pulverized) were added. The internal temperature of the solution was maintained at about 35° C. without stirring for 3 h (Note: if significant crystal formation on the flask surface was observed, occasional short (about 15 minutes) and strong agitation strokes were applied to break crystals on the flask surface). The mixture was slowly cooled to 20° C. at a rate of 1° C. per hour with no or minimal stirring. The internal temperature of the mixture was maintained at about 20° C. for 10-18 h. The product was collected by filtration as white needle crystals and was washed with n-heptane (0.5 mL), and dried under the filtration vacuum conditions for about 2 h. The solids were collected onto a pre-weighed petri dish, and the petri dish was covered and placed into a vacuum oven (21-25° C. at 20 mmHg) for more than 18 h to afford crystalline Form A (75-80%).

XRPD analysis indicated that the material was crystalline with a pattern consistent with Form A.

Example 5

Crystalline, Form A material of 6-O-(4-dimethylaminoethoxy)cinnamoyl fumagillol (free base) was scaled up as follows:

A 20 mL round-bottom flask was equipped with a stir bar or mechanical stirrer and a reflux condenser (it is not needed to have the condenser connected to cold water supply; air cooling is typically enough for the crystallization purpose). In a separate small vial, 6-O-(4-dimethylaminoethoxy)cinnamoyl fumagillol (1 g) was dissolved in ethyl acetate (1 mL). The resulting solution was filtered through a PTFE 0.2 um filter into the aforementioned 20 mL round bottomed flask using nitrogen pressure. The vial was washed with ethyl acetate (0.25 mL), and the resulting solution was filtered through the same PTFE 0.2 um filter using nitrogen pressure into the flask containing the filtrate. n-Heptane (10 mL) was filtered through the same PTFE 0.2 um filter using nitrogen pressure into the flask containing the filtrate (Note: significant precipitation is observed during the addition of n-heptane to the ethyl acetate solution). The resulting mixture was slowly heated to about 50-55° C. (Note: complete dissolution is often seen between 35-40° C.). The solution was slowly cooled to 25° C., and this temperature was maintained with slow stirring for 3 h (Note: white precipitation crashes and stirring speed may need to be adjusted for efficient mixing). The mixture was slowly cooled to 20° C., and the internal temperature of the mixture was maintained at this temperature for 10-18 h. The product was collected by filtration as a white fluffy solid and was washed with n-heptane (0.5 mL), and dried under the filtration vacuum conditions for about 2 h. The solids were collected onto a pre-weighed petri dish, and the petri dish was covered and placed into a vacuum oven (21-25° C. at 20 mmHg) for more than 18 h to afford crystalline Form A (75-80%).

XRPD analysis indicated that the material was crystalline with a pattern consistent with Form A.

Example 6

Crystalline, Form A material of 6-O-(4-dimethylaminoethoxy)cinnamoyl fumagillol (free base) was scaled up as follows:

A 20 mL round-bottom flask was equipped with a stir bar or mechanical stirrer and a reflux condenser (it is not needed to have the condenser connected to cold water supply; air cooling is typically enough for the crystallization purpose). In a separate small vial, 6-O-(4-dimethylaminoethoxy)cinnamoyl fumagillol (1 g) was dissolved in toluene (about 1 mL). The resulting solution was filtered through a PTFE 0.2 um filter into the aforementioned 20 mL round bottomed flask using nitrogen pressure. The vial was washed with toluene (warm or room temperature, 0.25 mL), and the resulting solution was filtered through the same PTFE 0.2 um filter using nitrogen pressure into the flask containing the filtrate. n-Heptane (5 mL) was filtered through the same PTFE 0.2 um filter using nitrogen pressure into the flask containing the filtrate (Note: significant precipitation is observed during the addition of n-heptane to the toluene solution). The resulting mixture was slowly heated to about 50-55° C. (Note: complete dissolution is often seen between 35-40° C.). The solution was slowly cooled to 28° C., at which time seed crystal (1 mg, pulverized) was added. The internal temperature of the solution was maintained at about 28 without stirring for 3 h (Note: if significant crystal formation on the flask surface was observed, occasional short (about 15 minutes) and strong agitation strokes were applied to break crystals on the flask surface). The mixture was slowly cooled to 20° C. at a rate of 1° C. per hour with no or minimal stirring. The internal temperature of the mixture was maintained at about 20° C. for 10-18 h. The product was collected by filtration as white rod crystals and was washed with n-heptane (0.5 mL), and dried under the filtration vacuum conditions for about 2 h. The solids were collected onto a pre-weighed petri dish, and the petri dish was covered and placed into a vacuum oven (21-25° C. at 20 mmHg) for more than 18 h to afford crystalline Form A (65-75%).

XRPD analysis indicated that the material was crystalline with a pattern consistent with Form A.

Example 7

A crystalline version of 6-O-(4-dimethylaminoethoxy) cinnamoyl fumagillol (free base) was scaled up as follows: amorphous gum-/oil-like free base material from three different vessels was combined into a 500 mL round bottomed flask as seen in Table 3:

TABLE 3

| Vessel | Weight of sample removed | DIPE added initially | DIPE added for washing out vessel |
| --- | --- | --- | --- |
| Round bottomed flask | 13.94 g | 70 ml | 20 ml |
| Round bottomed flask | 14.16 g | 70 ml | 20 ml |
| 20 ml Vial | 0.46 g | 3 ml | 2 ml |

After the initial addition of diisopropyl ether to each vessel, the three vessels were heated to 50° C. whilst stirring at ca. 300 rpm and kept at this temperature until the majority of the material appeared to have dissolved. The solutions from each vessel were then transferred to a 500 mL round bottomed flask. A second addition of diisopropyl ether was then added to each vessel in order to dissolve the remaining material and wash out the vessels into the 500 mL round bottomed flask. After the combination of the material from the three vessels, the 500 mL round bottomed flask contained ca. 28.56 g material dissolved in ca. 185 mL diisopropyl ether. The flask was then heated to 50° C. whilst stirring at ca. 300 rpm and held at this temperature for approximately 10 minutes. This allowed for all material to dissolve completely. After remaining at 50° C. for 10 minutes, the solution was then cooled at a rate of ca. 1° C./minute whilst stirring at ca. 300 rpm. Once the temperature had cooled down to 30° C., 14.8 mg of crystalline material made as in, for example, Example 1 was added to the flask for seeding (the crystalline seeding material had been ground for ca. 1 minute using an agate mortar and pestle, before it was added to the flask as seed). As the cooling continued down to 4° C., solid precipitated out of the solution until a thick slurry resulted. The flask was held at 4° C. for a further one hour whilst stirring at ca. 300 rpm. The material was then filtered and allowed to stand on the filter for approximately 10 minutes in order to dry. The material was then transferred to a beaker and placed into a vacuum oven (ca. 600 mbar) at ambient temperature (ca. 20° C.) in order to dry further. After remaining in the vacuum oven for 48 hours, the sample was weighed. $^1$H NMR analysis indicated the presence of ca. 2.4% residual solvent after drying for 48 hours. The sample was therefore dried for a further 3 days (i.e., 5 days of drying in total) under vacuum (ca. 600 mbar) at ambient temperature (ca. 20° C.). After the further drying was carried out, $^1$H NMR analysis indicated the presence of 1.13% residual solvent. The sample was then dried for a further 3.5 days (i.e., 8.5 days of drying in total) under vacuum (ca. 600 mbar) at 30° C.

Figure 9:
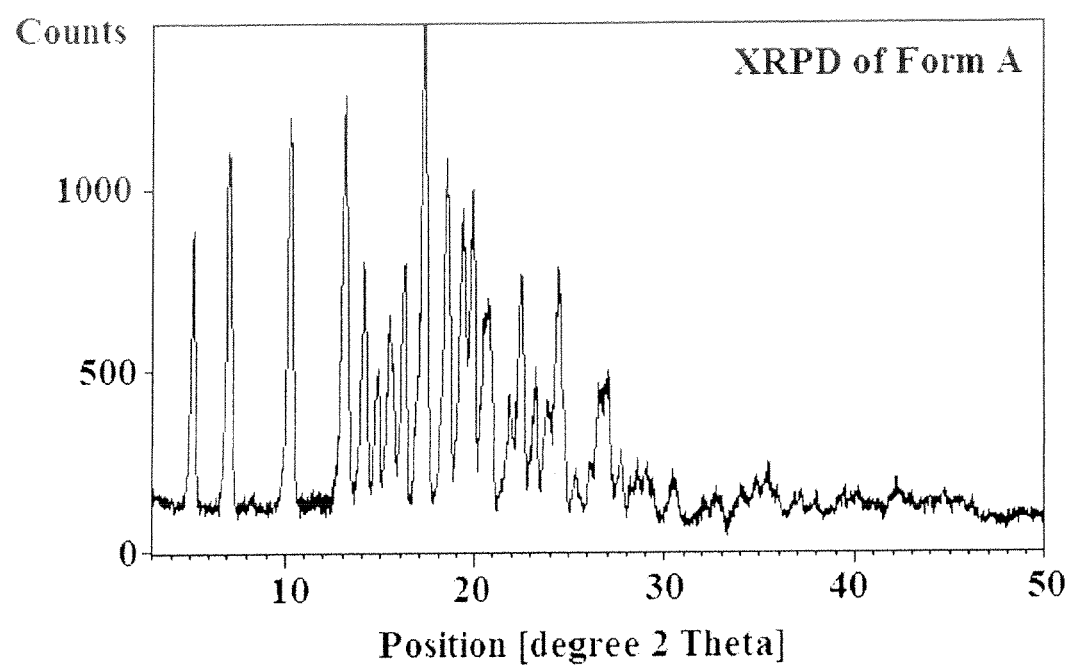
FIG. 9 is a X-ray diffraction pattern of Form A.

$^1$H NMR analysis was then carried out and no trace of residual solvent could be identified. HPLC analysis indicated purity of greater than 99.5%. XPRD is shown in FIG. 9.

Example 8

A crystalline version of 6-O-(4-dimethylaminoethoxy) cinnamoyl fumagillol, free base, was scaled up from fumagillol as follows:

In a 5 L glass reactor, toluene (1.5 L), fumagillol (300 g), 1-ethyl-3-(3-dimethylaminopropyl)-carbodiimide (EDC; 375 g (87.9%)), N,N-dimethylaminopyridine (DMAP; 261 g), and 4-[(2-N,N-dimethylamino)ethoxy]cinnamic acid (501 g) were added to the reactor in that order at room temperature. The mixture was heated from 20° C. to about 45-58° C. over 30 minutes, and stirred at that temperature for another 1-3 h until the reaction was complete. Reaction completion was monitored by thin-layer chromatography (dichloromethane:methanol (4:1), silica plate, anisaldehyde visualization) with less than 1% of fumagillol present (Note: the reaction typically requires between 2-3 h for completion).

After the reaction was confirmed to be completed, the mixture was cooled to 20-25° C. over 35 minutes and toluene (1.5 L) was added. The resulting mixture was filtered through a celite pad (300 g) to remove all undissolved materials and the celite pad was washed with toluene (3.0 L). The combined filtrate (6.85 L) was quantitatively analyzed by HPLC (520 g (97%) of the desired product was estimated present in the filtrate solution).

The toluene filtrates were washed pH 4.0-4.5, 250 mM ammonium acetate buffer solution (2 washes, 4.5 L per wash). The ammonium acetate buffer solution was prepared by dissolving ammonium acetate (174 g) in purified water (9 L) and adjusting the pH by addition of acetic acid (283 g). After confirming the removal of most of the DMAP and cinnamic acid (thin layer chromatography analysis (dichloromethane: methanol (4:1), anisaldehyde visualization)), the organic phase was washed with 5% NaHCO$_3$ (1.5 L) and purified water (1.5 L). An HPLC analysis was performed and no DMAP was detected.

Activated carbon (30 g, Nuchar SA-20) was added to the toluene solution and the mixture was stirred for 20 minutes. The activated carbon was removed by filtering the suspension through a celite pad (300 g) over 20 minutes, and the filtrate solution was filtered through a 0.2 um filter (Waters, Catalog No. 186003524) over another 20 minutes. The toluene solution was concentrated using a rotary evaporator in vacuo (bath temperature=35-40° C., 15-25 mbar), and the $^1$H NMR of the concentrate was taken to determine the residual toluene as 15.3%.

To the concentrate, n-heptane (1.0 L) was added and the resulting mixture was reconcentrated in vacuo (bath temperature=35-40° C., 15-25 mbar) over 25 minutes (product turned into a lumpy solid). The residual toluene in the concentrate was determined as 0% from $^1$H NMR analysis.

To this concentrate was added toluene (0.3 L filtered through a 0.2 um filter) and n-heptane (1.2 L filtered through a 0.2 um filter) and the resulting mixture was slowly heated to 40-51° C. over 40 minutes, resulting in complete dissolution of the solid. The mixture was slowly cooled to 25-36°

C. and 45 mg of Form A seed crystal was added. The mixture remained at room temperature without agitation for 10-25 hours.

The product was collected by filtration and the filter cake was washed with n-heptane (300 mL of 0.2 um filtered), and dried at between 28-30° C. under vacuum (0.2-0.3 inch Hg) for 24 hours to provide a crystalline form of 6-O-(4-dimethylaminoethoxy)cinnamoyl fumagillol, free base (375 g, 70.6%), with 98-99% HPLC purity (The filtrate was concentrated to provide the filtrate concentrate (117 g), which had 80.9% purity by an HPLC analysis).

XRPD analysis indicated that the material was crystalline with a pattern consistent with Form A.

Example 9

Recrystallization of a crystalline version of 6-O-(4-dimethylaminoethoxy)cinnamoyl fumagillol (free base) was performed as follows:

A 250 mL round-bottom flask was charged with crystalline 6-O-(4-dimethylaminoethoxy)cinnamoyl fumagillol (free base; 19 g). Toluene (ca. 19 mL) was added and the reaction was slowly heated (ca. 1° C./minute) on a magnetic hotplate stirrer (with heating mantle) to ca. 55° C., whilst stirring (oval magnetic stirrer bar, length: 2.5 cm) at ca 150 rpm. After complete dissolution, heptane (ca. 171 mL, pre-heated to ca. 55° C.) was slowly added and solid material began to immediately precipitate out of solution. After 10 minutes of stirring, the precipitated solid had dissolved, however a small amount of yellow gum was present. The solution was transferred to a different round-bottom flask (250 mL, pre-heated to ca. 55° C.) in order to remove the gum. The transferred solution was allowed to stir slowly (ca. 150 rpm) in the new flask for ca. 5 minutes before the hotplate was turned off and the reaction naturally cooled from 55° C. down to ambient (ca. 22° C.). Solid material crystallized out of solution at ca. 28° C. After cooling to ambient (ca. 22° C.), slow stirring (ca. 150 rpm) of the slurry was continued for a further 3 hours. After 3 hours, the solid was filtered using a Buchner funnel (diameter: 7.7 cm) and Buchner filter flask (500 mL) connected to a small diaphragm pump. Double filter paper was used in the filter (filter paper diameter 5.5 cm). The material was allowed to dry on the filter for ca. 10 minutes. The solid material was then placed into a crystallisation dish with a large surface area (diameter 14 cm) and allowed to dry in a Gallenkamp vacuum oven under vacuum (pressure ca. 25 mbar, absolute pressure reading) at ambient (ca. 22° C.) for approximately seven days to provide a crystalline form of 6-O-(4-dimethylaminoethoxy)cinnamoyl fumagillol, free base (ca. 15.1 g, 79.4%).

XRPD analysis indicated that the material was crystalline with a pattern consistent with Form A.

Example 10

Figure 10:
FIG. 10 is a micrograph of Form A.
Figure 11:
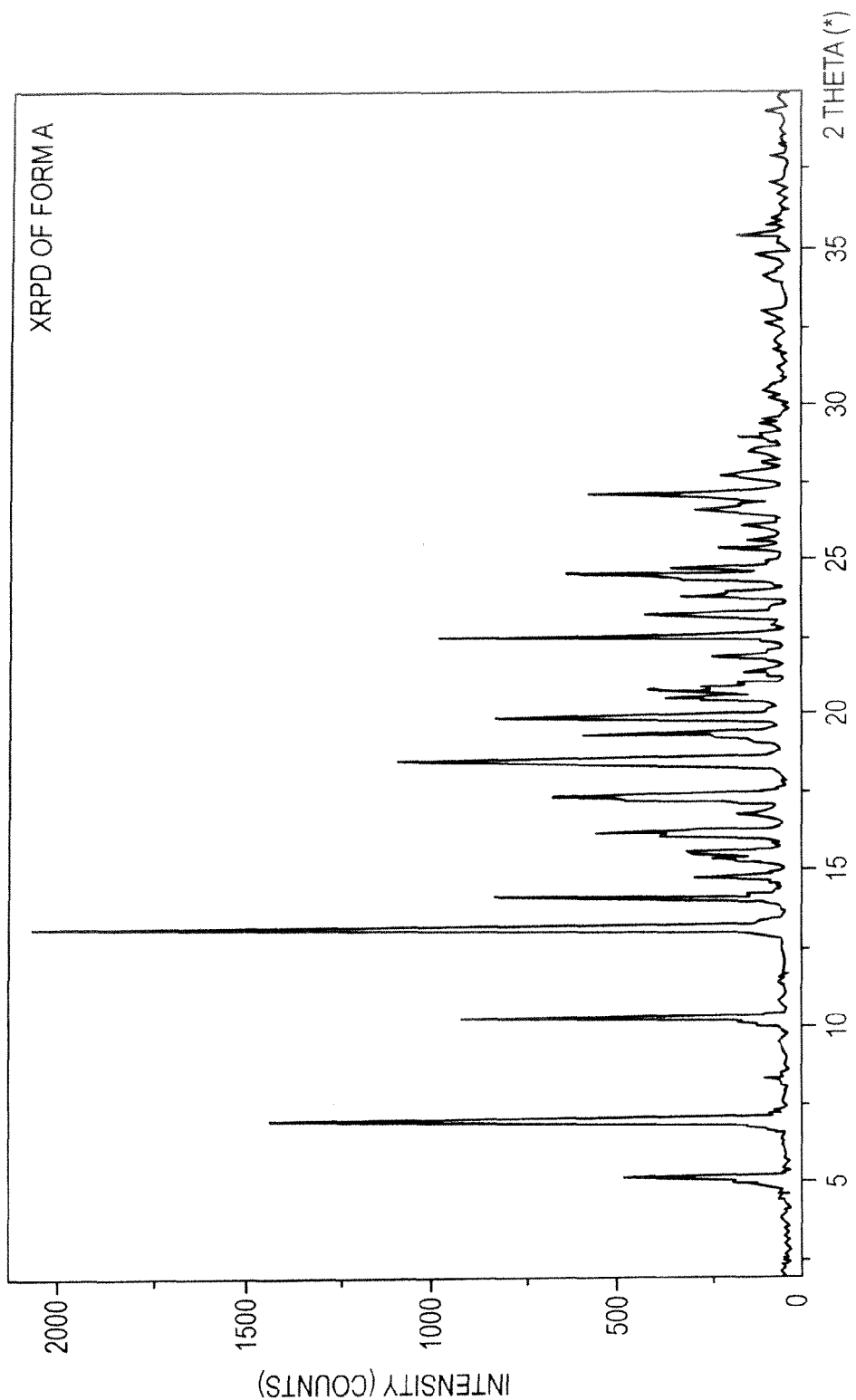
FIG. 11 is a X-ray diffraction pattern of Form A.

Crystalline material of 6-O-(4-dimethylaminoethoxy)cinnamoyl fumagillol (Form A) suitable for X-ray determination was prepared utilizing the solvent-antisolvent by vapor diffusion approach, as follows:

A filtered solution of Form A with a concentration of 100 mg/mL was prepared by stirring a sample of Form A (see FIGS. 10 and 11) in the appropriate amount of methyl-t-butyl ether at ambient temperature and then filtering the solution through a 0.7 μm glass fiber filter into a 1.2 mL vial insert. At this time, the filtered solution was exposed to vapors of pentane, resulting in the formation of crystalline material, which was submitted for single crystal structure determination. The single crystal structure determination procedure was conducted, as follows:

The single crystal sample of Form A was mounted on a Mitegen polyimide micromount with a small amount of Paratone N oil. All X-ray measurements were made on a Bruker-Nonius Kappa Axis X8 Apex2 diffractometer at a temperature of −163° C. The unit cell dimensions were determined from a symmetry constrained fit of 9994 reflections with 4.76°<2θ<55.5°. The data collection strategy was a number of ω and φ scans which collected data up to 59.34° (2θ). The frame integration was performed using SAINT (Bruker-Nonius, SAINT version 2009.9, 2009, Bruker-Nonius, Madison, Wis. 53711, USA). The resulting raw data was scaled and absorption corrected using a multi-scan averaging of symmetry equivalent data using SADABS (Bruker-Nonius, SADABS version 2009.9, 2009, Bruker-Nonius, Madison, Wis.).

The crystal structure was solved by direct methods using the XS program (Bruker-AXS, XS version 2009.9, 2009, Bruker-AXS, Madison, Wis. 53711, USA). All non-hydrogen atoms were obtained from the initial solution. The hydrogen atoms were introduced at idealized positions and were allowed to ride on the parent atom. The C3 atom site was disordered over 2 positions. The alternate position was designated C3'. The normalized occupancy for the primary position refined to a value of 0.698(10). The absolute structure could not be determined from the diffraction data. The absolute configuration of C14 was set to the absolute configuration (R) the corresponding atom (C6) reported in the structure of Fumagillin (Halász, J. et. al. *Tetrahedron*, 2000, 56, 10081). All other stereocenters were set relative to that assignment. The structural model was fit to the data using full matrix least-squares based on $F^2$. The calculated structure factors included corrections for anomalous dispersion from the usual tabulation. The structure was refined using the XL program from SHELXTL (Bruker-AXS, XL version 2009.9, 2009, Bruker-AXS, Madison, Wis. 53711, USA), graphic plots were produced using the NRCVAX crystallographic program suite.

Figure 12A:
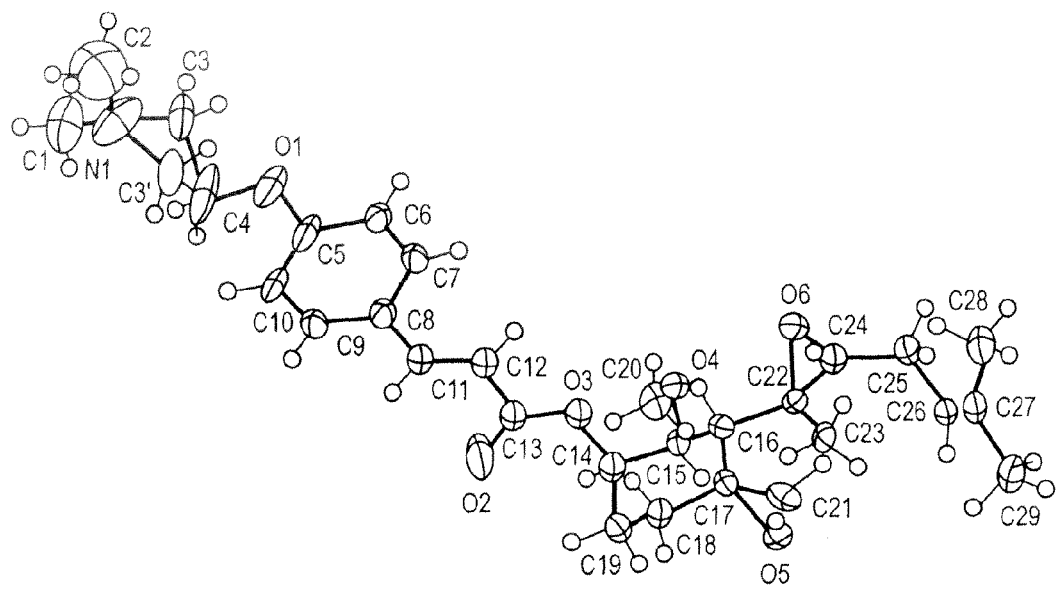
FIG. 12A is a ORTEP drawing of a Form A crystal.

The ORTEP drawing for the single crystal determination is shown in FIG. 12A. The summary of the crystal data is seen in Table 5, below.

TABLE 5

| | |
|---|---|
| Formula | $C_{29}H_{41}NO$ |
| Formula Weight (g/mol) | 499.63 |
| Crystal Dimensions (mm) | 0.43 × 0.15 × 0.06 |
| Crystal Color and Habit | colourless prism |
| Crystal System | orthorhombic |
| Space Group | $P\, 2_1\, 2_1\, 2_1$ |
| Temperature, K | 110 |
| a, Å | 6.2327(16) |
| b, Å | 13.118(4) |
| c, Å | 33.857(9) |
| α, ° | 90.00 |
| β, ° | 90.00 |
| γ, ° | 90.00 |
| V, Å$^3$ | 2768.2(13) |
| Number of reflections to determine final unit cell | 9994 |
| Min and Max 2θ for cell determination, ° | 4.76, 55.5 |
| Z | 4 |
| F(000) | 1080 |
| ρ (g/cm) | 1.199 |
| λ, Å, (MoKα) | 0.71073 |
| μ, (cm$^{-1}$) | 0.083 |
| Diffractometer Type | Bruker-Nonius Kappa Axis X8 Apex2 |
| Scan Type(s) | omega and phi scans |
| Max 2θ for data collection, ° | 59.34 |
| Measured fraction of data | 0.991 |
| Number of reflections measured | 56971 |
| Unique reflections measured | 4338 |

TABLE 5-continued

| | |
|---|---|
| $R_{merge}$ | 0.0435 |
| Number of reflections included in refinement | 4338 |
| Cut off Threshold Expression | >2sigma(I) |

Figure 12B:
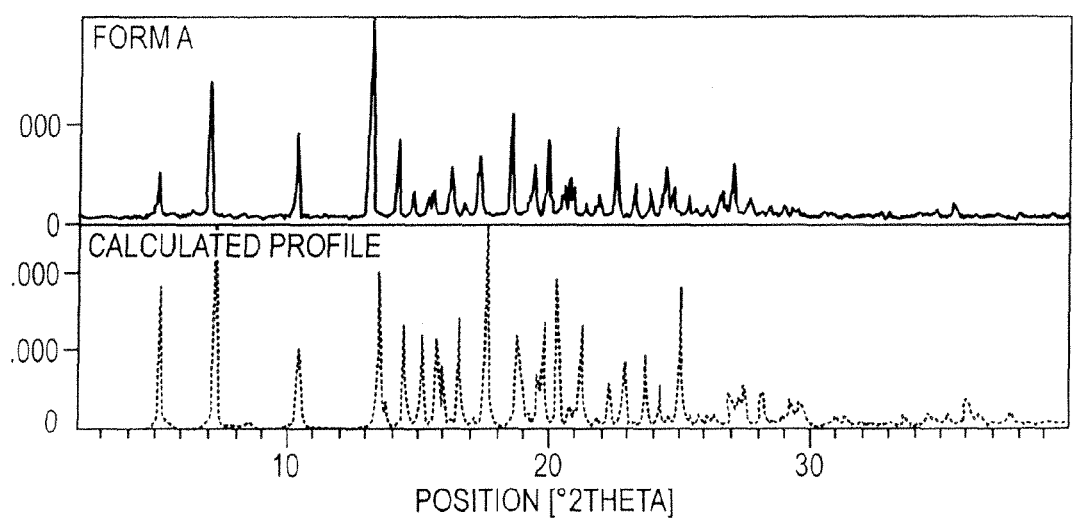
FIG. 12B is a comparison of the X-ray diffraction pattern of Form A at room temperature and the pattern calculated from the single-crystal data obtained at 110 K, and FIG. 12C are the atomic coordinates used to construct the ORTEP drawing of FIG. 12A.

The data for the crystal structure of the ORETP drawing of FIG. 12A is shown in FIG. 12C. A comparison of the X-ray diffraction pattern of Form A at room temperature and the pattern calculated from the single-crystal data obtained at 110 K is shown in FIG. 12B.

Example 11

Crystalline, Form C material of 6-O-(4-dimethylaminoethoxy)cinnamoyl fumagillol was prepared as follows:

Amorphous material was prepared by dissolving 6-O-(4-dimethylaminoethoxy)cinnamoyl fumagillol (20 mg) in methanol (0.5 mL), and placing the resulting solution in a centrifuge evaporator for 4 h. The amorphous phase can be detected using Raman spectroscopy, wherein the amorphous material displayed characteristic peaks at 1633 and 1707 cm$^{-1}$, while Form A displayed related peaks at 1627 and 1700 cm$^{-1}$.

Figure 13:
FIG. 13 is a micrograph of Form C.

A sample of amorphous material of 6-O-(4-dimethylaminoethoxy)cinnamoyl fumagillol was exposed to vapors of neat trichloroethane at ambient temperature. The amorphous form readily deliquesced. The deliquesced sample was stored in a cold environment and evaporated to dryness using a Genevac centrifuge evaporator. The sample was then sealed, submerged in dry ice for ca. 15 minutes and stored in a freezer (ca. 25° C.). The sample remained glassy during storage in the freezer (−20° C., 9 days), and was then stored at 5° C. (9 days), resulting in crystalline, Form C (see FIG. 13 for micrograph). A portion of the Form C sample was left at ambient temperature. The sample at ambient temperature, as well as the sample stored at 5° C., converted to Form A after three days. Form C was observed to be metastable relative to Form A.

Figure 14:
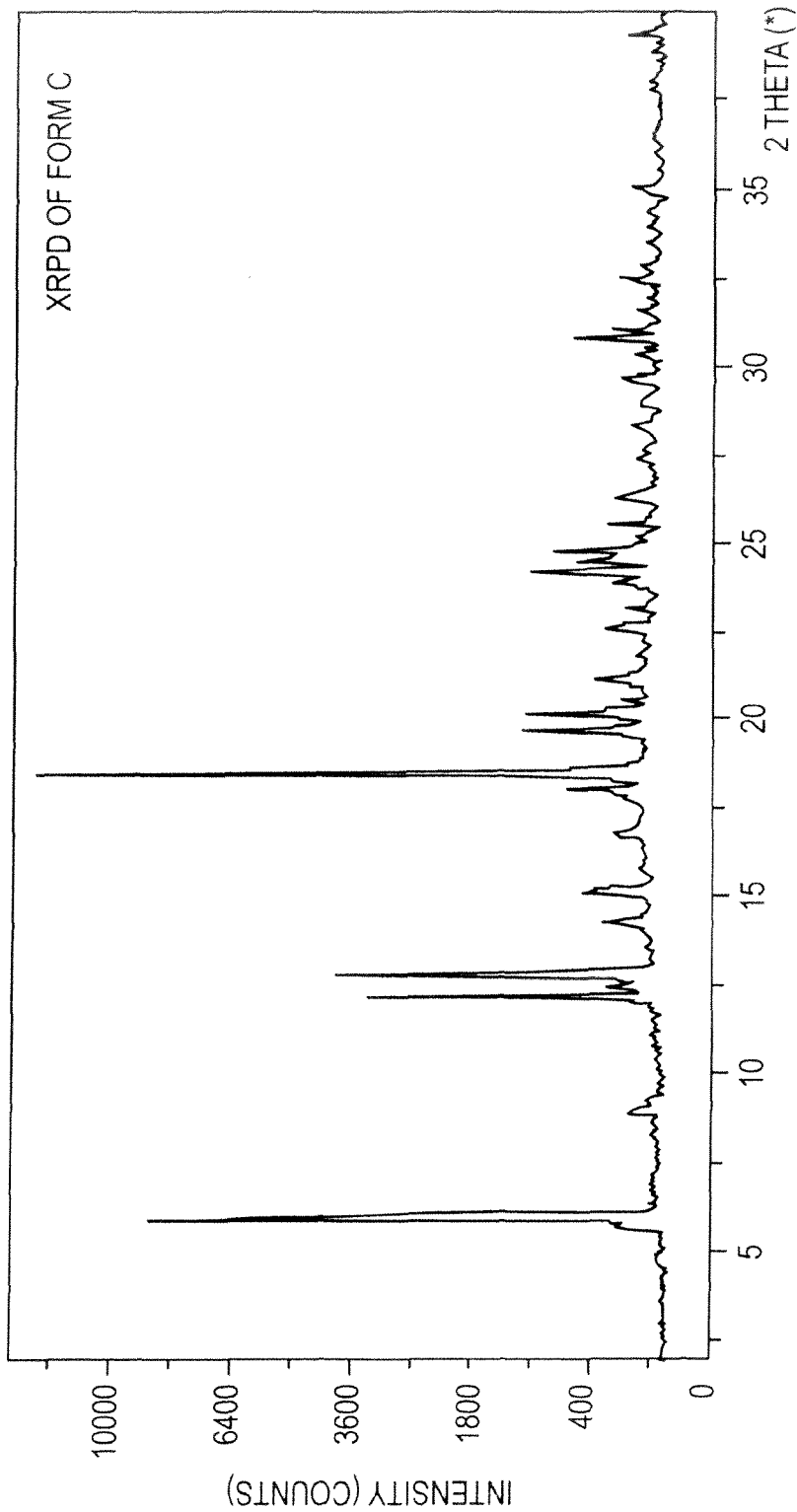
FIG. 14 is the X-ray diffraction pattern of Form C.

X-ray powder diffraction (XRPD) analysis was conducted on the solid crystals (Form C). XRPD analysis was carried out on a Bruker D8 Discovery diffractometer with a HI-STAR GADDS detector or on a PANalytical X'Pert Pro diffractometer on Si zero-background wafers. All diffractograms were collected using a monochromatic Cu Kα (45 kV/40 mA) radiation and a step size of 0.02° 2θ. The XRPD is shown in FIG. 14. The XRPD pattern of Form C does not show any of the characteristic peaks of Form A, and is though to be phase-pure.

Characteristic XRPD peaks include one or more of the peaks shown in Table 4, below.

TABLE 4

| Position [°2Th.] | d-spacing [Å] |
|---|---|
| 18.4 | 4.8 |
| 6.1 | 14.6 |
| 12.9 | 6.8 |
| 12.8 | 6.9 |
| 18.6 | 4.8 |
| 12.2 | 7.2 |
| 19.7 | 4.5 |
| 20.2 | 4.4 |
| 24.1 | 3.7 |
| 24.7 | 3.6 |

Infra-red spectroscopy was carried out on a Nicolet 6700 spectrometer (Thermo Electron) equipped with a DTGS detector and a Durascope. Spectra were obtained using the following parameters: 4 cm$^{-1}$ resolution, 64 scans, using Happ-Genzel apodization function and 2-level zero-filling.

Figure 15:
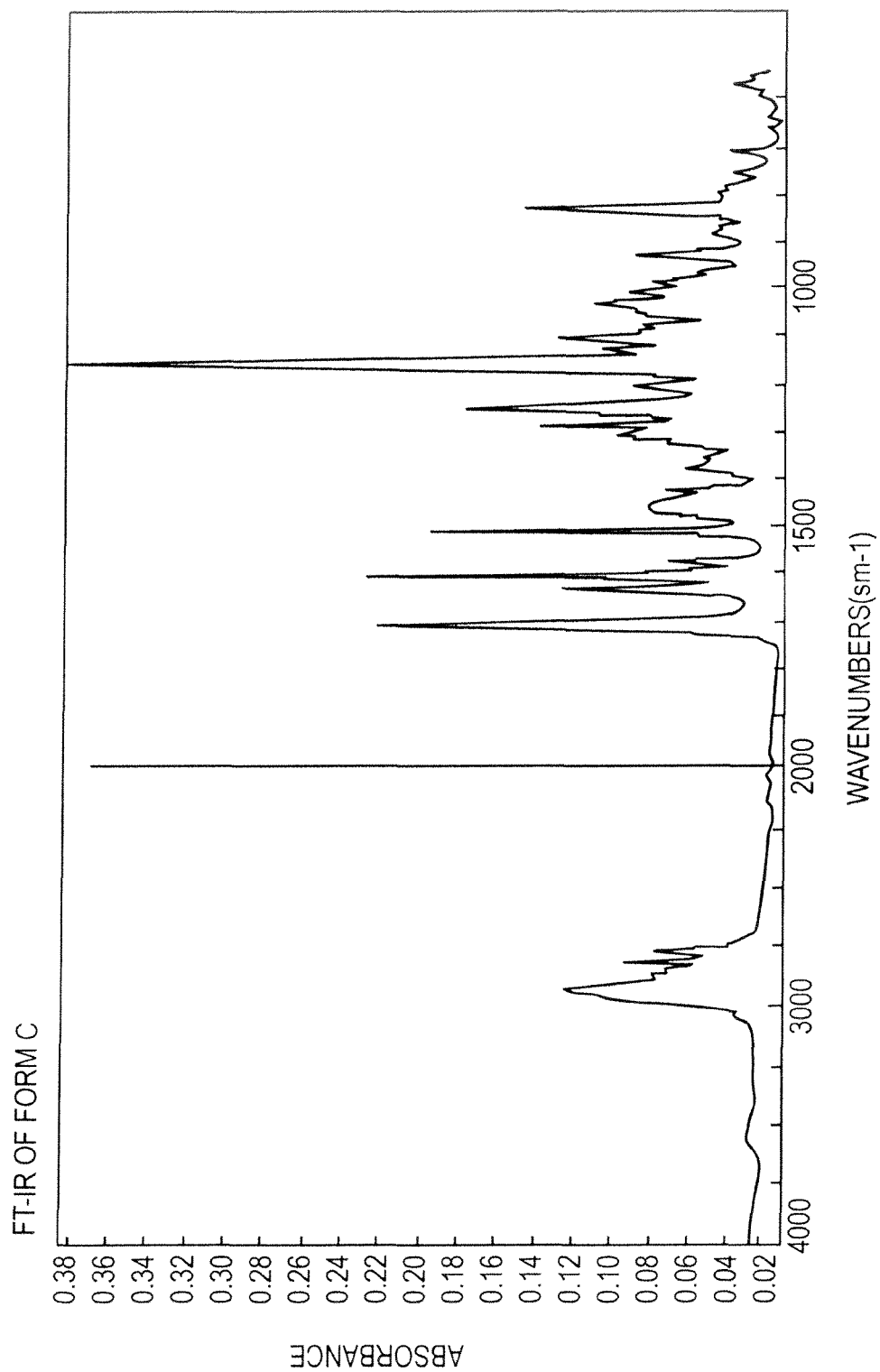
FIG. 15 depicts the FT-IR spectrum of Form C.

FIG. 15 depicts the IR spectrum of the prepared crystalline, Form C compound. As seen in FIG. 15, the IR spectrum of Form C shows peak shifts relative to Form A. For example, in the carbonyl region Form C shows a peak at 1707 cm$^{-1}$, while Form A shows a corresponding peak at 1700 cm$^{-1}$. In another example, Form C shows a peak at 894 cm$^{-1}$, while Form A does not show a similar peak in the fingerprint region.

Characteristic IR peaks include one or more of the peaks shown in Table 5, below.

TABLE 5

| FT-IR Absorption Bands, cm$^{-1}$ |
|---|
| 1159 |
| 1602 |
| 1707 |
| 1512 |
| 1249 |
| 831 |
| 1287 |
| 1106 |
| 1631 |
| 894 |

Raman spectroscopy was conducted utilizing a Nicolet NXR9650 or NXR 960 spectrometer (Thermo Electron) equipped with 1064 nm Nd:YVO$_4$ excitation laser, InGaAs and liquid-N$_2$ cooled Ge detectors, and a MicroStage. All spectra were acquired at 4 cm-1 resolution, 64-128 scans, using Happ-Genzel apodization function and 2-level zero-filling.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A pharmaceutical composition comprising a crystalline form of 6-O-(4-dimethylaminoethoxy)cinnamoyl fumagillol, free base, wherein the composition is a suspension of the crystalline form in a pharmaceutically acceptable carrier, wherein the crystalline form is characterized by a powder X-ray diffraction pattern having a characteristic peak in degrees 2θ at about 13.3, 17.4, and 19.9.

2. The pharmaceutical composition of claim 1, wherein the crystalline form of 6-O-(4-dimethylaminoethoxy)cinnamoyl fumagillol, free base, is characterized by a powder X-ray diffraction pattern having characteristic peaks in degrees 2θ at about 7.1, 13.3, 16.3, 17.4, 18.6, 19.4, and 19.9.

3. The pharmaceutical composition of claim 2, wherein the crystalline form of 6-O-(4-dimethylaminoethoxy)cinnamoyl fumagillol, free base, is characterized by a powder X-ray diffraction pattern having characteristic peaks in degrees 2θ at 5.2, 7.1, 10.4, 13.3, 14.2, 16.3, 17.4, 18.6, 19.4, and 19.9.

4. The pharmaceutical composition of claim 1, wherein the crystalline form of 6-O-(4-dimethylaminoethoxy)cinnamoyl fumagillol, free base, is characterized by the powder X-ray diffraction pattern shown in FIG. 1.

5. The pharmaceutical composition of claim 1, wherein the powder X-ray diffraction pattern was obtained using Cu Kα radiation.

6. The pharmaceutical composition of claim 1, wherein the pharmaceutically acceptable carrier is an aqueous carrier.

7. A method of treating obesity in a patient in need thereof, comprising subcutaneously administering to the patient an effective amount of the pharmaceutical composition of claim 1.

* * * * *